US005574212A

United States Patent [19]
Madsen et al.

[11] Patent Number: 5,574,212
[45] Date of Patent: Nov. 12, 1996

[54] AUTOMATED SYSTEM AND METHOD FOR TESTING RESOLUTION OF ULTRASOUND SCANNERS

[75] Inventors: Ernest L. Madsen; James A. Zagzebski; Gary R. Frank; Jason J. Rownd, all of Madison, Wis.

[73] Assignee: Wisconsin Alumni Research Foundation, Madison, Wis.

[21] Appl. No.: 490,319

[22] Filed: Jun. 14, 1995

[51] Int. Cl.⁶ .................................................. G01N 29/00
[52] U.S. Cl. ............................................ 73/1 DV; 73/618
[58] Field of Search ........................... 73/570, 618, 619, 73/640, 1 DV

[56] References Cited

U.S. PATENT DOCUMENTS

| | | |
|---|---|---|
| 4,277,367 | 7/1981 | Madsen et al. . |
| 4,286,455 | 9/1981 | Ophir et al. . |
| 4,331,021 | 5/1982 | Lopez et al. . |
| 4,406,153 | 9/1983 | Ophir et al. . |
| 4,417,582 | 11/1983 | Trimmer et al. ....................... 73/1 DV |
| 4,463,592 | 8/1984 | Flax et al. ............................... 73/1 DV |
| 4,476,549 | 10/1984 | Dragonette et al. .................... 73/1 DV |
| 4,843,866 | 7/1989 | Madsen et al. . |
| 5,276,726 | 1/1994 | Galkin ..................................... 378/207 |
| 5,312,755 | 5/1994 | Madsen et al. . |

FOREIGN PATENT DOCUMENTS

2814336  5/1979  Germany .

OTHER PUBLICATIONS

Smith, et al., "A contrast–detail analysis of diagnostic ultrasound imaging", Med. Phys., vol. 9, No. 1, pp. 4–12, Jan./Feb. 1982.

Madsen, et al., "An Anthropomorphic Ultrasound Breast Phantom Containing Intermediate–Sized Scatterers", Ultrasound in Med. & Biol., vol. 8, No. 4, pp. 381–392, 1982.

Madsen, et al., "Anthropomorphic Breast Phantoms for Assessing Ultrasonic Imaging System Performance and for Training Ultrasonographers: Part 1", J. Clin. Ultrasound, vol. 10, pp. 67–75, Feb. 1982.

Madsen et al., "Anthropomorphic Breast Phantoms for Assessing Ultrasonic Imaging System Performance and for Training Ultrasonographers: Part II", J. Clin. Ultrasound, vol. 10, pp. 91–100, Mar. 1982.

Goldstein, et al., "Particle Image–resolution Test Object", J. Ultrasound Med., vol. 2, pp. 195–209, May 1983.

(List continued on next page.)

Primary Examiner—Richard Chilcot
Assistant Examiner—Max H. Noori
Attorney, Agent, or Firm—Foley & Lardner

[57] ABSTRACT

In accordance with the present invention there is presented an automated system for testing the ability of clinical ultrasound scanners to detect focal lesions in human tissue. An ultrasound scanner phantom containing background material mimicking the ultrasonic characteristics of human tissue and coplanar spherical target lesions ultrasonically contrasting with the background material is scanned using the ultrasound scanner to be tested. Digitized images are made of the ultrasound scan of slices in the ultrasound phantom containing background material only and of slices on which the focal lesions are centered. A lesion signal to noise ratio $(SNR)_L$ is then calculated at each defined pixel coordinate in the target lesion slice. This calculation employs (1) a pixel value average calculated over a sample area of the target image slice centered at a pixel location and which is of a size approximately that of the cross-sectional area of the target lesions, (2) an average pixel value calculated over an averaging area centered at the same pixel coordinate but containing mostly background image data, and (3) a standard deviation of averaged pixel values calculated in the background material image plane. The proximal and distal depth range limits of detectability of an ultrasound scanner, for a given lesion diameter and contrast, may then be determined based on the number of pixel locations in a depth range of the scanned plane having an absolute value SNR greater than a threshold value.

29 Claims, 6 Drawing Sheets

OTHER PUBLICATIONS

Wagner, et al., "Statistics of Speckle in Ultrasound B–Scans", IEEE Trans. on Sonics and Ultrasonics, vol. 30, No. 3, pp. 156–163, May 1983.

Smith, et al., "Low Contrast Detectability and Contrast/Detail Analysis in Medical Ultrasound", IEEE Trans. on Sonics and Ultrasonics, vol. 30, No. 3, pp. 164–173, May 1983.

Goodsitt, et al., "A Three Dimensional Model for Generating the Texture in B–Scan Ultrasound Images", Ultrasonic Imaging, vol. 5, pp. 253–279, 1983.

Madsen, et al., "Method of data reduction for accurate determination of acoustic backscatter coefficients", J. Acoust. Soc. Am., vol. 76, No. 3, pp. 913–932, Sep. 1984.

Smith, et al., "Frequency Independent Ultrasound Contrast–Detail Analysis", Ultrasound in Med. & Biol, vol. 11, No. 3, pp. 467–477, May/Jun. 1985.

Wagner, et al., "Unified SNR analysis of medical imaging systems", Phys. Med. Biol., vol. 30, No. 6, pp. 489–518, 1985.

Thijssen, et al., "Gray Level Transforms and Lesion Detectability in Echographic Images", Ultrasonic Imaging, vol. 10, pp. 171–195, 1988.

Thijssen, et al., "Texture in Tissue Echograms", J. Ultrasound Med. vol. 9, pp. 215–229, 1990.

Lopez, et al., "Objective Analysis of Ultrasound Images by Use of a Computational Observer", IEEE Trans. on Med. Imaging, vol. 11, No. 4, pp. 496–506, Dec. 1992.

Insana, et al., "Visual detection efficiency in ultrasonic imaging: A framework for objective assessment of image quality", J. Acoust. Soc. Am., vol. 95, No. 4, Apr. 1994.

AUTOMATED SYSTEM AND METHOD FOR TESTING RESOLUTION OF ULTRASOUND SCANNERS

FIELD OF THE INVENTION

This invention pertains generally to the field of ultrasound scanners, and more particularly to the testing of the resolution capabilities of such scanners using imaging phantoms as test objects.

BACKGROUND OF THE INVENTION

An ultrasound scanner is an integrated device which includes a scanning head and cooperating mechanical and electronic components, including a signal detection apparatus, for producing an ultrasound image. An ultrasound image is the result of a complicated set of physical phenomena, namely, the absorption, reflection, and coherent scattering from a tissue medium of pulsed radio frequency ultrasonic pressure waves, and the electronic detection of the backscattered or echo pulses for display as an image. The resulting pictures have a granular structure variously described by the terms texture or speckle. The resolution capability of an ultrasound scanner is its capacity to produce an image distinguishing a target object in a scanned volume, known as a slice, from the texture in the image produced from adjacent background material. An object which is resolved may be said to be detected by an ultrasound scanner. Typically, the signal detection apparatus of an ultrasound scanner includes a monitor for displaying a visual image. To be resolved, when only such a monitor is in use, an object must be detectable by an examination of such an image.

The resolution of target objects in a clinical ultrasound scan is possible because of the ultrasonic differentiation of tissue structures, primarily through variations in the scattering of ultrasonic waves by these tissues. This diffuse scattering gives rise to the texture pattern of an ultrasound image of a clinical object where variations in gray level are seen in the displayed image. Often, the mean gray level of a displayed object of interest, e.g. a tumor, will be different from that of the surrounding tissue. In other words, there is displayed image contrast between the object of interest and the background. The displayed image contrast is associated with the object contrast between the material of the object of interest and the background material. The object contrast, in turn, is a function of the difference, or ratio, of the backscatter coefficients of the two media involved, one for the object of interest material, the other for the background material.

Detectability of an object in an ultrasound image depends on three factors: (1) the size of the object, (2) the object contrast, and (3) the nature of the texture or speckle pattern of the object with respect to its background surroundings. The first two factors are determined by the material being imaged, whereas the third factor is strongly dependent on the scanner instrumentation. Thus, the smaller the object the less detectable, or resolvable, it is. At the same time, the less the object contrast, the less detectable the object is. Object contrast is based on the backscatter coefficients of the material of the object of interest, the target object or lesion, and the surrounding background material. Object contrast may be defined, in decibels, to be:

$$C = 10 \log_{10}(\eta_1/\eta_b) \quad (1)$$

where:

C is the object contrast;

$\eta_1$ is the backscatter coefficient of the target lesion material; and $\eta_b$ is the backscatter coefficient of the surrounding background material.

The resolution performance of ultrasound scanners may be tested using ultrasound test objects known as phantoms. Most current commercially available phantoms for testing performance of ultrasound scanners contain a uniform background material which is tissue mimicking in terms of ultrasonic attenuation, propagation speed and backscatter coefficient. Such a material is described in U.S. Pat. No. 4,277,367, to Madsen, et al., entitled "Phantom Material and Method." A variety of types of phantoms are used to determine the resolution abilities of ultrasound scanners. Most of these phantoms containing objects to be detected. For example, one type of phantom contains metal or plastic fibers, arranged either individually or in pairs, oriented perpendicular to the scanning plane. An ultrasound scanner is thereby tested by its ability to detect the fibers at all, and also by a determination of the least separation between fibers such that they can still be resolved.

Another type of phantom consists of a block of gelatin containing long, thin cones or, alternatively, stepped cylinders of gelatin. Both the block of gelatin, and the target cones or cylinders within it, contain plastic beads or other particles that function as ultrasound scatterers. Each stepped cylinder contains scatterers of a different size and/or concentration relative to the scatterers contained in the background material so that the scattering level of the background material is different from that of each cylinder. The cylinders, therefore, have a controlled object contrast level. During use, the axes of the cone or cylinder shaped target objects are maintained at right angles to the scanning plane (the plane of symmetry of the scanned slice).

The cylindrical geometry of the target objects in the phantom just described results in a nearly constant object contrast being maintained over the intersection of the target cylinder with the scan slice. A shortcoming of such a geometry is that the ultrasound slice profile does not provide for a realistic determination of detectability of a target when the diameter of the cylinder is in the range of, or less than, the slice width. This is because there is almost never a clinical situation in which an object of interest has translational symmetry perpendicular to the scan plane. Thus, since no attempt is made to approximate the three-dimensional shape of the lesions commonly being searched for in clinical applications of ultrasound scanning, the significant effect of the width of the slice on detectability is not dealt with. Thus, tests involving cylindrical targets do not adequately evaluate an ultrasound scanner regarding detection of focal lesions.

It has, therefore, been recognized that a focal lesion is realistically represented with a sphere. U.S. Pat. No. 4,843,866, to Madsen, et al., entitled Ultrasound Phantom, describes an ultrasound phantom including testing spheres having backscatter coefficients different from the backscatter coefficient of the tissue mimicking material in which they are embedded. In that invention, the testing spheres are located within the phantom body in a random array in order to eliminate the possibility of user bias when resolution characteristics are being tested by human observers. Another embodiment of that invention includes a phantom body divided into multiple subsections. Each subsection may contain testing spheres differing in size or backscatter coefficient from those in the other subsections.

Evaluations of ultrasound scanner performance have been made using a phantom in which a large number of spherical simulated lesions are randomly distributed as described above. For example, these phantoms were used to assess focal lesion detectability performance of various ultrasound scanner configurations. Estimations were made by a group of human observers of the proximal (shortest) distance from the scanning head where lesions may first be resolved, and distal (farthest) distance from the scanning head where lesions become no longer resolvable, to ascertain the limits of the depth range over which lesions of a given size and contrast were detectable. This depth range of detectability may be referred to as the resolution zone. For a given image depth and object contrast there will be a minimum lesion diameter which is resolvable and for which detection exists. A graph of the contrast versus the minimum diameter of lesion detectable at a certain depth is the contrast-detail curve at that depth. Thus, if the proximal and distal limits of the depth range are known for a sufficiently broad range of lesion diameters and contrasts for a certain imager configuration, this is equivalent to knowledge of the contrast-detail curves at all depths.

There are, however, shortcomings to this method for determining the proximal and distal limits of the depth range of detectability. Firstly, the process for estimation of the proximal and distal depth ranges by an observer can be time-consuming, especially if a reasonably large set of combinations of target lesion diameters and contrasts are involved. Secondly, estimations of the proximal and distal limits of the depth range can depend on the experience of the human observer.

Therefore, although ultrasound phantoms such as those described make possible many different types of performance measurements, it is still uncommon for clinical personnel to obtain specifications, make purchase decisions, and evaluate ultrasound scanners using quantitative image performance criteria. They rely almost solely on clinical impressions when judging the performance of a scanner. A more automated method for determining focal lesion detectability would nullify these limitations, and, consequently, foster much more widespread use of these types of resolution tests.

A computer-based method for the analysis and evaluation of ultrasound images is presented in a paper by Hector Lopez, et al., "Objective Analysis of Ultrasound Images by Use of a Computational Observer", IEEE Transactions on Medical Imaging, Vol. 11, No. 4, pp. 496–506, 1992. This method employs the concept of a "matched filter" with ultrasound phantoms containing low contrast cone-shaped and essentially cylindrical targets to do objective contrast-detail studies. This matched filter technique is conceptually simple when the target object is basically cylindrical in shape, with axial symmetry of mean object contrast along the cylinder, and where the cylinder is oriented perpendicular to the ultrasound scan slice. The first step of this method is the making of an ultrasound scan image of a slice perpendicular to the cylindrical target, which is then digitized. The digital image is then sectored, and location coordinates for each target object in the image are established. The signal to noise ratio (SNR) of the target object is then calculated. A SNR cut-off point may then be established, with lesions having a SNR above the threshold considered detectable, or resolved, and those below the threshold considered not detectable.

A lesion signal to noise ratio calculated by the matched filter method, $(SNR)_{ML}$, is defined as:

$$(SNR)_{ML} \equiv (S_{ML} - S_{MB})/(\sigma_B^2 + \sigma_L^2)^{1/2}. \tag{2}$$

Note that $(SNR)_{ML}$ does not represent a simple pixel signal to noise ratio but depends on the size of the target lesion whose detectability is being analyzed. In Equation 2, $S_{MB}$ reflects an average of pixel values of an image of the phantom background material. $S_{MB}$ is the ensemble average of a large number of independent realizations of $S_B$, which is defined as:

$$S_B \equiv (1/n) \sum_{i=1}^{n} P_i^m \tag{3}$$

$S_B$ is the mean of the mth power of the image pixel values over the projected (usually circular) area of the focal lesion in the image plane in an area known to contain no lesions (background). In other words, the digitized image is first examined and the area which should be occupied by a known lesion is determined. This area will contain n pixels, each having a pixel value $P_i$. $S_B$ is then calculated over an area of n pixels in a portion of the image plane which contains background material only, and no lesions. $S_{MB}$ is then the average of a large number of independent calculations of $S_B$ over several such n pixel areas in areas of the image containing background material only.

This calculation may be made using either the "amplitude" or the "intensity" value of each pixel in the area containing n pixels. If m=1, then $P_m$ is called the pixel amplitude, and $S_B$ is called the pixel amplitude mean. If m=2, then $P^m$ is called the pixel intensity, and $S_B$ is called the pixel intensity mean.

In Equation 2, $S_{ML}$ reflects an average of the average pixel values of an image of the phantom lesion material. That is, $S_{ML}$ is the ensemble average of $S_L$ for independent realizations of $S_L$ where:

$$S_L \equiv (1/n) \sum_{i=1}^{n} W_L(r_i) P_i^m \tag{4}$$

$S_L$ is the weighted mean of the mth power of the image pixel values over an area in the image corresponding to the known location of lesion. As discussed above, this area will contain n pixels, each having a pixel value $P_i$. $S_L$ is then calculated over this same n pixel area of the image known to correspond to the position of a target lesion. $S_{ML}$ is then the average of independent calculations of $S_L$ over multiple n pixel areas in a set of images which are statistically independent. In other words, the speckle patterns in the ensemble of images must be statistically independent. This means that independent physical realization of the target lesions and background material must be used. If the simulated lesions are cylinders oriented perpendicularly to the scanning slice, then the images (and speckle patterns) will be statistically independent if the scan slices do not overlap one another.

$W_L(r_i)$, in Equation 4, is a weighting function of the distance, $r_i$, from the center of the circular target area over which $S_L$ is being calculated. This factor depends on the expectation value of $P_i$ relative to that of the background material. If $W_L(r_i)$ is independent of the distance from the center of the lesion area, $r_i$, corresponding to an infinitely long cylinder with uniform ultrasonic properties, including backscatter coefficient, then $W_L(r_i)=1$.

The final two components of Equation 2 are $\sigma_B$ and $\sigma_L$. $\sigma_B$ is the standard deviation of the ensemble of $S_B$ values, and $\sigma_L$ is the standard deviation of the ensemble of $S_L$ values.

SUMMARY OF THE INVENTION

The present invention presents an automated system and method for determining the lesion resolution capability of an ultrasound scanner system. The system of the invention includes one or more ultrasound phantoms. Each phantom has a body made of ultrasonic tissue mimicking material.

The phantom body is preferably divided into multiple sections. In the sections of the phantom body arrays of target spheres, representing target lesions, are embedded in the body material, with the spheres in each array having preferably coplanar centers. The spheres in each array are of the same diameter and object contrast. The array is arranged so that many spheres exist in the image plane per centimeter of depth, or distance from the phantom scanning window. The spheres are preferably distributed from the scanning window of the phantom from a depth of about, for example, 0.5 centimeters to a depth of about 15 centimeters. A range of sphere diameters and contrasts may be represented in a single phantom. One section of the phantom preferably contains only background, or reference, tissue mimicking material.

In carrying out the method of the invention, an ultrasound scan of the phantom is made using a scan slice centered along a plane of the phantom in which an array of spheres having the same diameter and contrast are present. One or more similar scans are also made of the region of the phantom containing only background material. The images are then digitized and stored in permanent computer memory, such as on a hard disk. The digitization of the gray levels in the ultrasound image generally should be such that the resulting pixels are small enough that subsequent resolution determinations are not compromised.

The system of the invention then uses the image data to determine the detectability of a target sphere in the image. In the present invention, the exact position of the sphere in the image plane need not be known. It may be noted that without such knowledge, calculation of pixel value averages over the target area as required by the prior basic matched filter method, is not possible. The invention employs a modification of the matched filter method which determines signal to noise ratios for the ultrasound scan images using a scan technique in which pixel value averages and standard deviations (or variances) are calculated for each defined pixel location in an image plane over averaging areas including the pixel location and containing only or mostly background material. Similarly, pixel value averages are calculated for corresponding pixel locations over an area centered at each defined pixel location in the image plane which contains target lesions. No such calculations are made for pixel locations near (e.g., within 5 mm of) the outer edge of the image. These pixel locations are considered not defined because they lack sufficient surrounding pixel locations to allow averages of averages to be made in the region of the central pixel location. The only knowledge of the target lesion locations which is required is that their centers be approximately coplanar in the image plane. Since complex alignment procedures are not required, the system may be used by clinical personnel trained in the operation, rather than service personnel trained in the diagnosis, of ultrasound scanner systems. From the calculated pixel value averages and standard deviations of these averages, a modified lesion signal to noise ratio $(SNR)_L$ is calculated for each defined pixel location in the target lesion image plane.

The lesion signal to noise ratio $(SNR)_L$ calculated in accordance with the present invention is different from $(SNR)_{ML}$ calculated in accordance with Equation 2, in that the ensemble pixel value average $S_{ML}$ is replaced by a single realization of pixel value averages in the target lesion image plane, $S_L$. The ensemble average concept of the matched filter method is recovered via the fact that many identical lesions are represented in the image over each increment in image depth (e.g., of 0.5 cm to 1.0 cm). Also in accordance with the present invention, the standard deviation of lesion pixel averages, $\sigma_L$, may be set equal to the standard deviation of background pixel average, $\sigma_B$, for ease of computation, without significantly changing the final results.

The system preferably also determines the number of defined pixel locations in the scan image, within given depth ranges, having SNRs beyond a certain threshold value. This histogramatic data is then employed by the system, using a second threshold value, to determine the proximal and distal limits of the depth range over which lesions of a given size and contrast are detectable by the ultrasound imager. The threshold values may have been previously chosen to optimize agreement of the automatic system results with average proximal and distal depth range values for human observers. The resulting proximal and distal depth range values may then be used to compare the performance of various ultrasound scanners in resolving lesions of various sizes and contrasts.

The automated analysis system of the present invention allows a clinical user to obtain rapidly a realistic user-independent estimate of the focal lesion detection performance of any scanning equipment configuration. The automatic analysis system can be used by nontechnical clinical personnel for comparison of various imager configurations, including a particular scanner, transducer, and collection of scanner settings, corresponding to a given imaging situation. Thus, the clinician can be better acquainted with imager capabilities which may not be apparent from superficial indications, such as focus depth. The automated system of the present invention can also be employed as one way for comparing imagers when decisions must be made regarding purchase of an imager. Imager purchase specifications and acceptance testing may employ the automated system, and the automated system may also be used as part of a periodic quality assurance program. In the latter case, the choice of some limited number of combinations of lesion diameter and contrast may be specified to make the tests sufficiently brief. The fact that spherical simulated lesions in the imaging phantom relate more readily to clinical imaging than resolution fibers and cylinders provide needed motivation for clinical personnel to carry out quality assurance on a regular basis. The system may also be used for personnel training in ultrasound. Ultrasound scanner manufacturers can also employ the present invention for quality assurance testing and in equipment refinement.

Further objects, features, and advantages of the invention will be apparent from the following detailed description when taken in conjunction with the accompanying drawings.

DETAILED DESCRIPTION OF THE INVENTION

Figure 1:
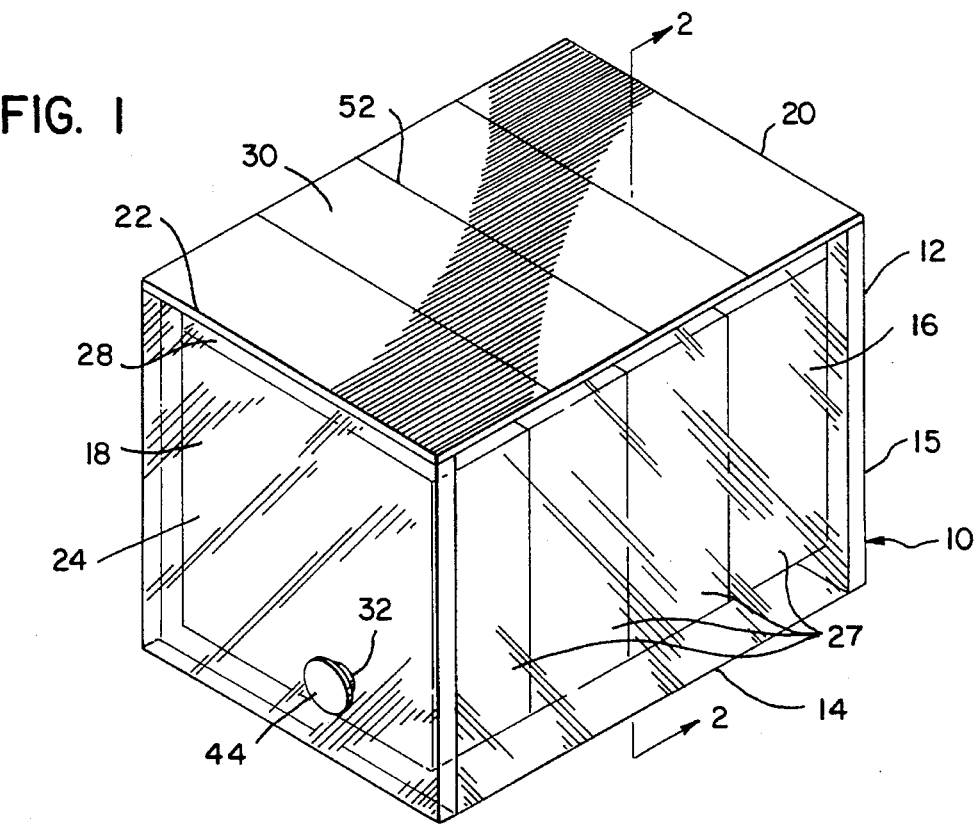
FIG. 1 is a perspective view of an ultrasound phantom having multiple body sections.

A preferred ultrasound phantom which is used for the ultrasound testing system and method of the present invention is shown generally at 10 in FIG. 1. The ultrasound phantom 10 includes a container 12 having a bottom 14 and walls 15. Preferably the walls 15 include opposed faces 16, and opposed ends 18. Taken together, the bottom, faces, and ends 14, 16 and 18 form a hollow, box-like structure. Margins of the walls 15 remote from the bottom 14 define a window 20. The window 20 is closed with an ultrasound-transmitting window cover 22. The window cover 22 may be made of any cohesive ultrasound transmitting material of suitable physical durability. A thin sheet of polyurethane or saran is preferred.

The ultrasound phantom 10 further includes a phantom body 24. The phantom body substantially fills the container 12 up to the level of the window 20. The phantom body 24 includes a material exhibiting ultrasound characteristics that mimic animal soft tissue. A material shall be deemed to mimic animal soft tissue if, when compared to the corresponding ultrasound characteristics of the selected animal soft tissue, its attenuation coefficient differs by no more than 10%, its ultrasonic speed by no more than 1%, its specific gravity by no more than 10%, and that its backscatter coefficient is within the same order of magnitude.

At least in theory, the more exactly these characteristics of the tissue mimicking material correspond to those of animal soft tissue, the more precisely will results obtained by ultrasound scanning of the phantom allow the user of the phantom to predict the scanning characteristics of the same equipment when used on animal soft tissue. A suitable and preferred tissue mimicking material is an agar gel, with selected solid particles dispersed throughout the agar to adjust the attenuation and scatter coefficients thereof. Such a tissue mimicking material is disclosed in U.S. Pat. No. 4,277,367, the disclosure of which is incorporated herein by reference. The ultrasonic characteristics of this material are preferably adjusted to have a density of approximately 1.03 g/ml, an attenuation coefficient slope of approximately 0.5 dB/cm/MHz, and an ultrasonic speed of approximately 1540 m/s.

The phantom body 24 may also include scattering particles having a diameter such that their presence increases the backscatter coefficient of the material. To be effective, scattering particles must be large enough so that measurable ultrasonic scatter occurs and small enough, and sufficiently closely spaced, that the texture pattern displayed by the ultrasound scanner being tested does not represent resolution of individual scattering particles. Glass beads have been found acceptable for use as scattering particles, with the diameter of the glass beads preferably being not less than 20 microns and not greater than 100 microns.

The preferred phantom body material just described contains water, and is subject to drying by escape of the water to the atmosphere, which can result in changes in acoustic properties that make the material a less effective tissue mimicker. Consequently, when such a material is used, the container 12 must be liquid tight and preferably also water vapor tight. The window cover 22 must include means for reducing water transfer therethrough. To this end, the window cover 22 may be made of a flexible plastic material that does not readily transmit water vapor. An alternative means for reducing water transfer through the window cover 22 includes a layer 28 of an oil based gel that completely closes the window 20, adhering to the uppermost portions of the faces 16 and ends 18 in water and water vapor-tight relation. The layer 28 of oil-based gel preferably is also covered with a thin and flexible plastic sheet 30 that serves to form and protect the surface of the layer 28 of oil-based gel.

In practice, the bottom 14, faces 16 and ends 18 of the phantom 10 may be molded as a unit or formed of flat pieces of plastic or other material which are glued or otherwise joined so as to constitute the container 12. At least one of the bottom 14, faces 16 or ends 18 includes a filling hole 32. Molten tissue mimicking material may be injected into the interior of the container through the hole 32 using a syringe (not shown). In any case, the container 12 should be entirely filled with material, with all air bubbles removed. After the material forming the phantom body 24 has solidified, the syringe may be removed from the container 12 and the filling hole 32 closed by any convenient means, such as a stopper 44.

The phantom body 24 may be divided into generally rectangular, box-shaped subsections 27. (The vertical lines shown in the face 16 of the phantom 10 of FIG. 1 are only to help illustrate the different definable sections 27 of the phantom body 24; they are not meant to imply that there are actual physical vertical divisions in the phantom body material.) Each subsection 27 extends between the opposing faces 16. Within each subsection 27, the phantom body 24 includes a tissue mimicking material as described above. Furthermore, the phantom body subsections 27 include arrays of testing spheres, as will be described in more detail below. Preferably, one of the subsections 27 has no testing spheres whatsoever, i.e., it contains only tissue mimicking background material. The other sections 27 preferably contain sphere arrays that include spheres which are different in size or ultrasound contrast characteristics from the spheres in the other subsections. A more detailed description of the construction and operational use of an ultrasound phantom as generally described above may be found in U.S. Pat. No. 4,843,866, the disclosure of which is incorporated herein by reference.

A focal lesion in human tissue, such as a tumor, is most realistically represented as a sphere. This is because the ultrasonic detection of a target object depends on all three dimensions of resolution. For example, consider a clinical target object having low contrast, such as a tumor, with an irregular 3-dimensional boundary. An ideal 2-dimensional ultrasound image would depict the object with an outline corresponding to the intersection of the scanned plane, with an ideal zero slice thickness, with the 3-dimensional tumor boundary. Since the actual scan slice thickness is never zero, there will be blurring of this ideal 2-dimensional image outline. Therefore, accounting for elevational resolution corresponding to the dimension perpendicular to the scanning plane, is crucial. Thus, as was discussed earlier, the use of essentially cylindrical target objects, which are nearly uniform in the elevational direction, to measure contrast detectability is inferior to using spherical target objects.

For this reason, spherical target objects are used in the imaging phantom 10. The testing spheres may be most conveniently made of the same agar gel based material as the phantom body background material 24. However, a different concentration of scattering particles is used in the spheres to create an acoustical contrast between the spheres and the background body material 24. When agar is used in the material selected to make the testing spheres, the agar may be made up in molten form, with the scattering particles mixed therein. The spheres may be conveniently molded in a two-part, split mold of conventional design (not shown). It is preferable that testing spheres of various diameters and object contrasts should be made. For example, 3 millimeter and 4 millimeter diameter spheres may be made with contrasts of −15, −9, −6 and +3 db for each size of sphere. Other combinations of sphere diameter and contrast may also be used. Increasing the range of diameters and contrasts of target spheres used for images analyzed by the system will increase the reliability of analysis results when making comparisons between scanner systems or configurations, for example. The object contrast of the various spheres is controlled through the concentration of glass bead scatterers which are distributed in the tissue mimicking background material and the material which makes up the testing spheres. The background material may preferably contain 45–53 micrometer glass bead scatterers at a concentration of a few grams per liter of material. The concentration of glass bead scatterers for the −6 db target lesions, for example, would be ¼th that of the background material. The resulting testing spheres should have the same basic ultrasonic characteristics, except for backscatter coefficient, as the background material. The tissue mimicking material is selected such that the object contrast does not depend on the frequency of the ultrasound scan. This is guaranteed by using glass bead scatterers with the same diameter distribution in the background and in the target lesions.

Figure 2:
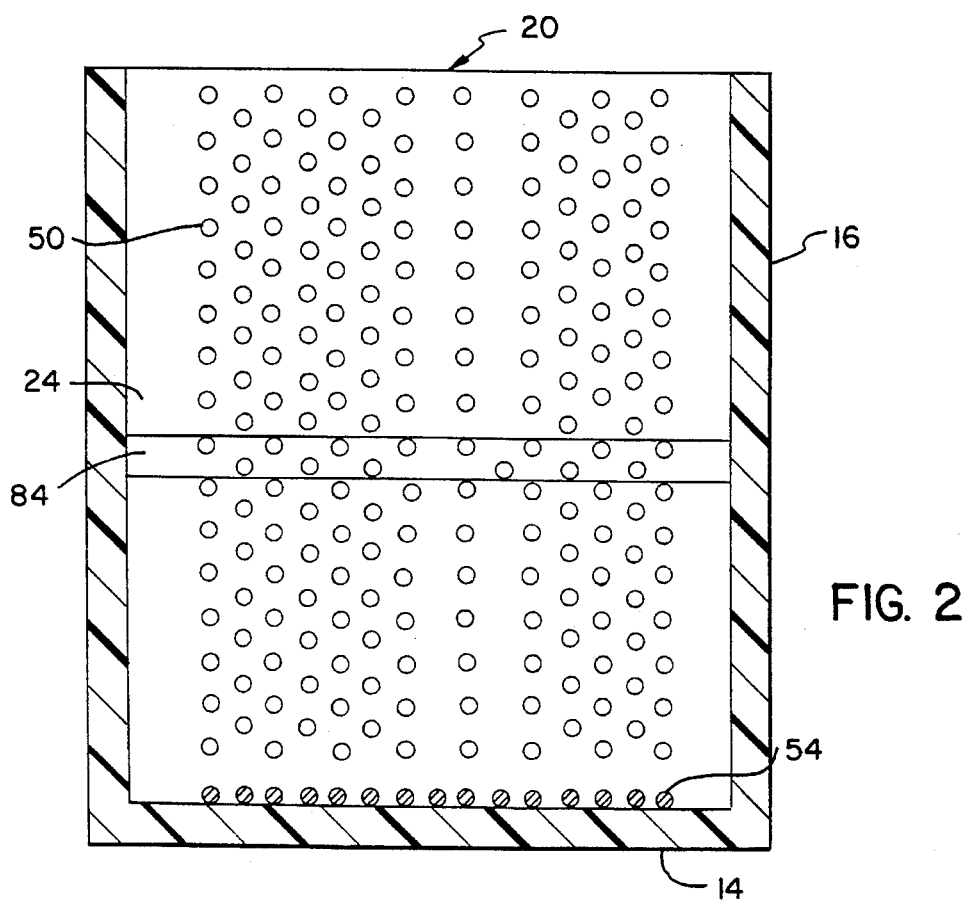
FIG. 2 is a cross-sectional view through an ultrasound phantom showing two regular arrays of target spheres of the same diameter, and with coplanar centers, distributed through the phantom body.

For each diameter and object contrast, the target spheres 50 are positioned in a regular array in a section 27 of the phantom body 24, with their centers approximately coplanar so that the ultrasound transducer can be arranged with all spheres centered in the scan slice. FIG. 2 is a cross-section through an ultrasound phantom such as is shown in FIG. 1, illustrating regular arrays of target spheres 50 as just described. The window cover 22, oil-based gel layer 28, and flexible plastic sheet 30 of FIG. 1 are not shown in FIG. 2 for simplicity. Two arrays of spheres 50, each array having the same diameters, are shown in FIG. 2. The spheres of each array preferably have a different characteristic such as contrast level. The arrays of spheres preferably extend from a depth of, e.g., about 0.5 centimeters below the scanning window 20 to a depth of about 16 centimeters. For each 1 centimeter increment in depth, there are 7 identical spheres in each array. The objective is to have statistically significant numbers of spherical focal lesions at all depths. Thus, the number of target lesions per centimeter of depth may be increased, for example, to 15 identical target lesions per centimeter of depth, for increased statistical accuracy. Additionally, a second scanning window may be incorporated into the bottom 14 of the ultrasound phantom to effectively double the number of independent focal lesions per centimeter of depth. Each subsection 27 of the phantom 10 shown in FIG. 1 may contain similar configurations of testing spheres in sets of regular arrays as shown in FIG. 2. The arrays will differ from each other in the size or object contrast of their spheres. At least one subsection of the phantom 10, as mentioned earlier, will contain only background material, however.

The same ultrasound phantom used for the automatic analysis system of the present invention may also be used for analysis of ultrasound scanner configurations using human observers. This is necessary for the determination of proper threshold values, described in more detail below, so that the automatic analysis results can be calibrated to correspond with the human observer based results. Human observers may, however, be influenced in their choices of proximal and distal limits of the resolution zone by the periodicity of target lesion placement. Thus, the phantoms may be made so that the distribution of target spheres in the plane is pseudo-random rather than regular. The spheres' centers will still preferably be coplanar and the number of spheres per centimeter of depth range must remain statistically significant. The spheres should be positioned such that no two spheres have their surfaces closer than one sphere diameter to discourage false positives.

Figure 3:
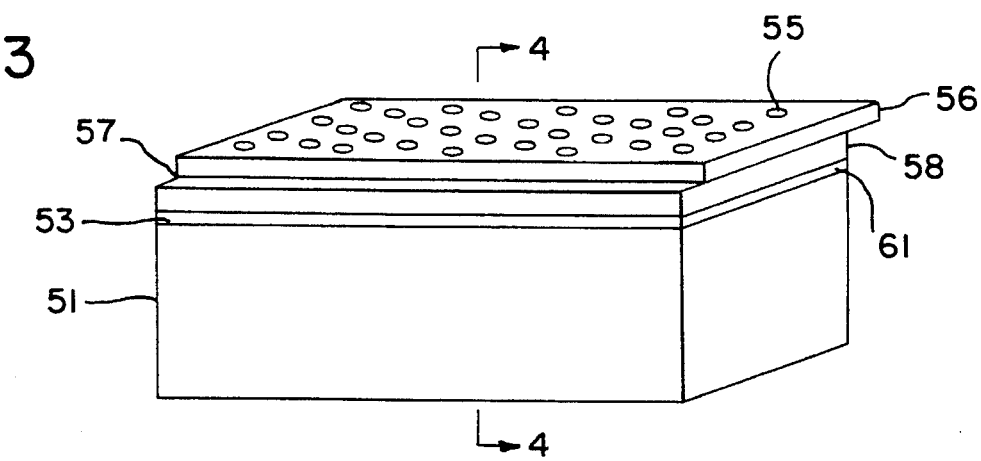
FIG. 3 is a perspective view of an apparatus for producing a coplanar array of target lesions in a section of an ultrasound phantom.
Figure 4:
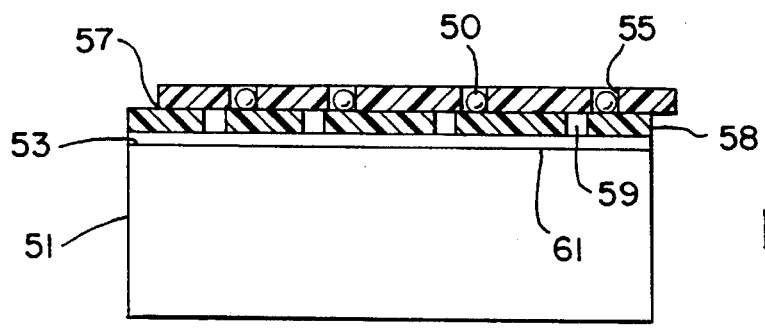
FIG. 4 is a cross-sectional view of the apparatus shown in FIG. 3.

A preferred method and apparatus for producing a coplanar array of target lesion spheres 50 in a section 27 of an ultrasound phantom 10 is described with reference to FIGS. 3 and 4. FIGS. 3 and 4 are not necessarily drawn to scale and are presented for explanatory purposes only. Part of a phantom section 51 is made in a mold from molten background material and allowed to solidify. The partial section 51 has an exposed planar side 53 on which the array of spheres 50 will rest, assuring that their centers will be coplanar. Target lesions 50 of the desired diameter and contrast are made in a conventional manner using a two-sided mold with opposing hemispherical depressions. The target spheres 50 are placed in cylindrical holes 55 through the top slab 56 of an array template 57. The template apparatus 57 also includes a bottom slab 58 with an array of holes 59 corresponding to the holes 55 in the top slab 86. The slabs 56 and 58 may preferably be made of ⅛ inch thick Lucite. The arrangement of the holes 55 and 59 corresponds to the arrangement of the array of spheres to be produced in the phantom section 27. As discussed above, the arrangement may be regular or random. The two slabs are in contact, and initially displaced so that spheres 50 placed in the top slab 56 will be constrained from falling through the holes 59 in the bottom slab 58. A thin layer 61 (e.g., 2–3 mm) of molten background material is quickly poured over the horizontal surface 53 of the solid partial section 51. While the molten layer is still liquid, the sphere-loaded template 57 is quickly positioned over the liquid layer 61. The slabs 56 and 58 are then displaced appropriately to line up the holes 55 and 59 of both slabs so that all of the spheres 50 fall through the holes 59 in the bottom slab 58 simultaneously. The spheres settle in the liquid layer 61 in the desired array pattern, the horizontal surface 53 of the solid partial section 51 constraining the spheres so that their centers are coplanar. The molten layer 61 fixes the positions of the spheres 50 when it congeals. If done quickly enough, no loss in uniformity of glass bead scatterers in the background material of the layer 61 due to gravitational settling will occur. The phantom section 27 is completed by enclosing the section half 51 in a mold (not shown), leaving a gap over the exposed surfaces of the spheres 50 as they project above the now solidified layer 61, and filling the gap with molten background material. Air is excluded from the mold using a syringe piston, and the mold is preferably rotated about a horizontal axis to prevent gravitational sedimentation of glass bead scatterers until the molten background material has congealed. Each section 27 may be made in this fashion, with the various sections combined to form a phantom as in FIG. 1.

To assist in the proper alignment of the ultrasound transducer with the plane of target spheres, lines 52 (see FIG. 1), which lie on the plane containing the sphere centers, are placed on the scanning window cover 30. The transducer (not shown) is positioned so that the scan plane (assumed to be the plane of symmetry of the scan head) passes through one of the lines 52. The transducer is then angled so that the scan plane is approximately parallel to the sphere plane and rotated slightly so that spheres appear to be detectable to the greatest depth. Another method for aligning the transducer is to place a row of spherical stainless steel reflectors 54 (see FIG. 2) distal to the simulated lesions so that the stainless steel sphere centers lie in the plane containing the simulated lesions. Alignment is achieved when echoes from the stainless steel spheres have been maximized. In a phantom with a scanning window on the top and bottom, the chain of stainless steel spheres could be positioned at the distal window and the phantom immersed in water for the scan. Alternatively, if two windows are desirable, they may be at right angles to one another. Two perpendicular rows of distal stainless steel spheres may then be embedded in the phantom opposite the windows.

Figure 5:
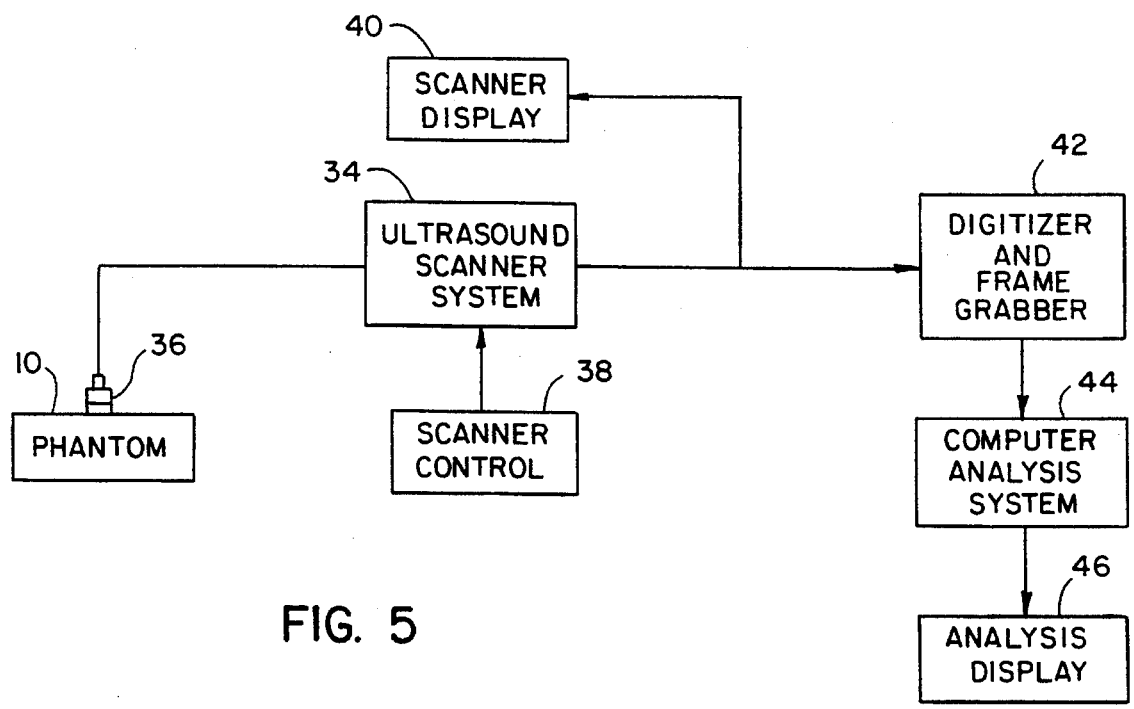
FIG. 5 is a block diagram of the automated system for testing the resolution capability of an ultrasound scanner of the present invention.

The method and system for employing the phantom just described to automatically determine the resolution characteristics of an ultrasound scanner will now be described with reference to FIG. 5. The ultrasound scanner system 34 includes a transducer or scanning head 36 which is placed in contact with the ultrasound transmitting window cover 22 of the phantom 10 for making an ultrasound image. Alternatively, a water bag (not shown) or any of the other spacers or surface conformation arrangements commonly used with diagnostic and other ultrasound scanning heads, may be placed between the transducer 36 and scanning window 22 to acoustically couple the transducer 36 to the phantom 20. A scanner control panel 38 allows for manual adjustment of the ultrasound scanner settings. The scan image produced by the scanner system 34 is displayed on a scanner display 40 such as a video monitor. A frame grabber and digitizer 42 is used to capture the ultrasound video image and convert the image to digital data which is stored in a computer analysis system 44. The computer analysis system 44 operates on the digital image data as described below to determine the resolution capabilities of the scanner system 34. The results of this analysis may be displayed on an analysis display 46 such as a monitor or printer.

The first step in the analysis process is the making of an ultrasound scan with the scan slice midplane superimposed on a plane of the phantom on which the target spheres are centered, i.e., the plane of symmetry of the scan slice is superimposed on the plane of the spheres. The scan is made with the scanner settings adjusted to achieve uniform average background brightness in the scanned image. The resulting image may be referred to as the lesion or target plane image. With the same scanner settings, an ultrasound scan is made of a slice through a subsection of the ultrasound phantom 10 which contains no spherical target lesions 50, but only background material. The resulting image may be referred to as the background plane image.

The video frame grabber 42 is used to make digitized images of the lesion and background plane images. The digitized image data is preferably stored in permanent computer memory, such as on a hard disk. The digitized gray level data preferably represents pixels which are small enough that subsequent resolution determinations are not compromised. For example, a Macintosh Centris computer equipped with a video frame grabber board, such as the Data Translation DT2255, may be used to acquire the digitized images. The frame grabber may be connected directly to the output video signal from the ultrasound scanner 34. The public domain software NIH Image may be used to both control the data acquisition sequence and select and store the image data on the computer hard drive. Either data representing an entire image or a region of interest on the image can be stored. Stored digitized image data and other data may be archived on a magneto-optical drive.

Image data from the Macintosh is transferred, such as via an ethernet connection, to, for example, a DECstation 5000/200 workstation computer running Ultrix 4.1 for image analysis. The Macintosh TIFF images may be converted to portable bit mapped images using XV version 3.00 on the analysis computer 44. Image analysis programs (e.g., written in C) are compiled and run on the analysis computer 44.

Analysis is accomplished using lesion plane image data, or data representing a portion of such an image, from a plane containing an array of coplanar spheres having the same diameter and contrast, e.g., one of the test sphere arrays shown in FIG. 2, and data from a corresponding background plane image containing no target lesions.

If the lesion image slice profile were known, i.e., the positions of the target lesions in the plane were known, then the matched filter method as discussed above could be applied with little compromise to spherical targets centered in the scan plane. However, if the slice profile is not known, which must be assumed in clinical situations, then the $W_L(r_i)$ value must be approximated. An example of a reasonable approximation follows. Let the radius of a spherical target lesion be r. The sphere can then be approximated to have a cylindrical shape of radius approximately equal to $(\frac{3}{4})r$ and length $2r$ where the axis of the cylinder is perpendicular to the scan plane. Note that the cylinder volume approximates the sphere volume. For programming convenience, the sphere may be approximated with a square-ended cylinder having length perpendicular to the scan plane which is approximately equal to $(\frac{3}{4})r$ and with the side of the square equaling $(\frac{4}{3})r$. The projected area of the sphere is then taken to be the area of the square. Thus, n is the number of pixels in the square area, and since the slice profile should not vary greatly over this projected area, $W_L(r_i)$ may be set equal to 1. An approximate matched filter process can now be defined for spherical lesions.

One way to apply the matched filter concept of Equation 2 would be to compute $S_{ML}$, $s_{MB}$, $\sigma_B$ and $\sigma_L$ at some depth in the image plane. Thus, independent realizations $S_L$ and $S_B$ at the depth involved would be required, where the area over which $S_L$ is computed would be centered at a known lesion location, requiring alignment procedures. Because the system of the present invention is intended for use by clinical personnel, and because the lateral and axial positioning of the spheres is not exact, although the sphere centers are definitely coplanar, a method has been devised for avoiding the need to know exactly where the lesions are in the scanned plane. This is done by adaptation of the $(SNR)_{ML}$ calculation to a computer scan technique.

A signal to noise ratio $(SNR)_{L(j,k)}$ is calculated at each defined pixel position (j,k) in the target image plane in accordance with the following Equation:

$$SNR_L(j,k) \equiv (S_L(j,k) - S_{MB}(j,k))/(\sigma_B(j,k)^2 + \sigma_L(j,k)^2)^{1/2} \quad (5)$$

where:

j and k are a set of pixel coordinates at the center of a square area on the lesion image plane and a corresponding area on a background image plane over which $S_L(j,k)$, $S_{MB}(j,k)$, $\sigma_B(j,k)$ and $\sigma_L(j,k)$ are computed. Notice that $S_L(j,k)$ is a single realization, not the ensemble average $S_{ML}$.

In applying the modified matched filter concept, the computation of $\sigma_B$ and $\sigma_L$ for each (j,k) pixel location could be prohibitive in terms of computational time required. Therefore, $\sigma_L$ is preferably set equal to the standard deviation of the ensemble of pixel value averages from the background plane, $\sigma_B$, for all object contrasts. If the object contrast is small, then setting $\sigma_L$ equal to $\sigma_B$ is clearly reasonable. However, setting $\sigma_L$ equal to $\sigma_B$ generally is a reasonable approximation even when object contrast is large since detectability thresholds are involved and the backscattered ultrasound signal from the surrounding background material spills over into the lesion area on the image. This phenomenon involves lateral and axial aspects of spillover in the case of cylinders which are perpendicular to the scan plane. There is an added effect in the case of spheres. Some background material will almost always exist in the volume which gives rise to the lesion signal since this is a cylindrical volume perpendicular to the scan slice which includes both the sphere volume and a partial volume of background material. Therefore, a partial volume effect will generally exist for spherical targets. Thus, for spherical lesions in the regions of the imaged area where lesions are barely detectable, the approximation is justified even when object contrast is large. Equation 5 may, therefore, be approximated by $$SNRL(j,k) = (S_L(j,k) - S_{MB}(j,k)) / (2^{1/2}) \sigma_B(j,k) \quad (6)$$

$S_L$ is computed over a square area centered at the (j,k)th pixel in the target image plane. The computation sampling area is preferably a square of side ⅔ times the known sphere diameter. $S_{MB}$ and $\sigma_B$ are computed over a square area which is preferably centered at, but must at least contain, the (j,k)th pixel on a corresponding image of mostly background material. Preferably $\sigma_B$ is calculated over the background plane image and $S_{MB}$ is calculated over the target plane image, though both may be calculated over the background plane image as well. $S_{MB}$ and $\sigma_B$ are preferably computed over a 1 cm² averaging area. Note that it is not necessary that $S_{MB}$ be strictly the ensemble average over areas corresponding to a lesion since, assuming some degree of uniformity of the slice profile, $S_{MB}$ is approximately equal to the mean pixel value over a sufficiently large image area. For example, for a 1 cm² averaging area, $S_{MB}$ is the pixel value average over an area which is equivalent to at least 100 mm²/9 mm² ≈11 independent ensemble elements for a 3 mm×3 mm lesion area. Thus, in this context, ensemble averaging refers to calculation of the average of the pixel value averages of multiple sampling areas, corresponding to the target lesion size, over the larger averaging area which includes many sampling areas. It should also be noted that using a large averaging area means that $S_{MB}$ calculated in the target image plane will still represent mostly background, rather than target, pixel values. $\sigma_B$ is then obtained by computing many values of $S_B$ corresponding to smaller sampling areas lying in the 1 cm² area in the background image plane. Multiple independent background images may be employed so $S_B$ may be computed over multiple realizations of each 1 cm² area. Better estimates of $\sigma_B$ result from the use of multiple background images than from one image, of course.

In the preferred automated system, $\sigma_B$ is determined using a set of pixel value averages obtained from a 1 cm² averaging area in a background only image containing the defined pixel location (j,k). However, the mean pixel value of background areas in the lesion containing image may be influenced by the average pixel value at lesion areas of the image. This is due to beam side-lobe effects. Thus, for example, for lesions of negative object contrast, which have a lower backscatter coefficient than the background material, the ensemble background average pixel value, $S_{MB}$, calculated in the lesion containing image may be less than $S_{MB}$ calculated using an image plane containing no background lesions whatsoever. It is for this reason that the preferred representation of $S_{MB}$ is the pixel average over an averaging area (e.g., 1 cm²) in the lesion containing image centered on the defined pixel location. Any error, resulting from lesions being represented in the averaging area, is offset by the correction for side lobe influences described.

Figure 6:
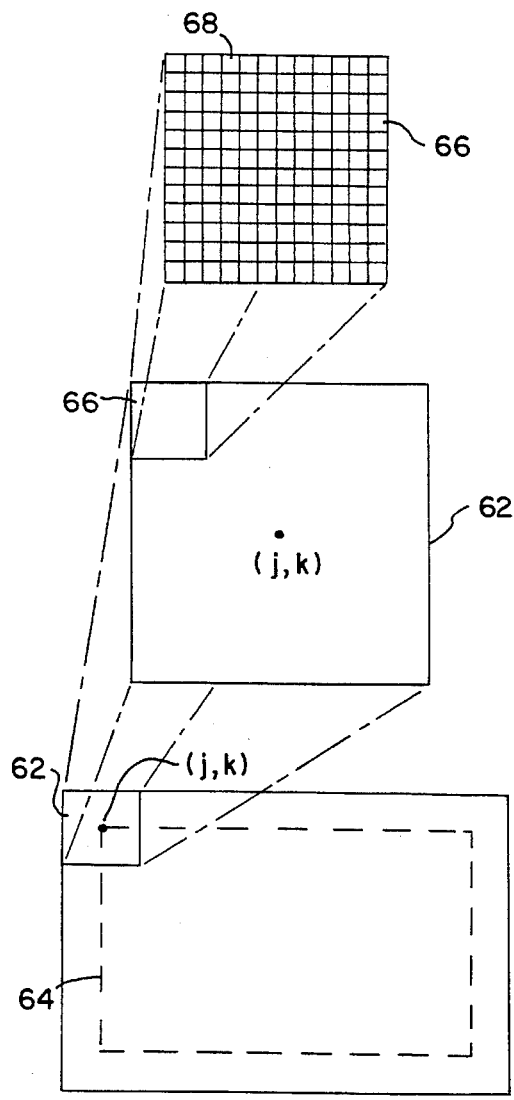
FIG. 6 is a series of illustrations of the areas and subareas of an image plane containing mostly background material over which average background pixel values and variances are calculated for a defined pixel location (j,k).
Figure 7:
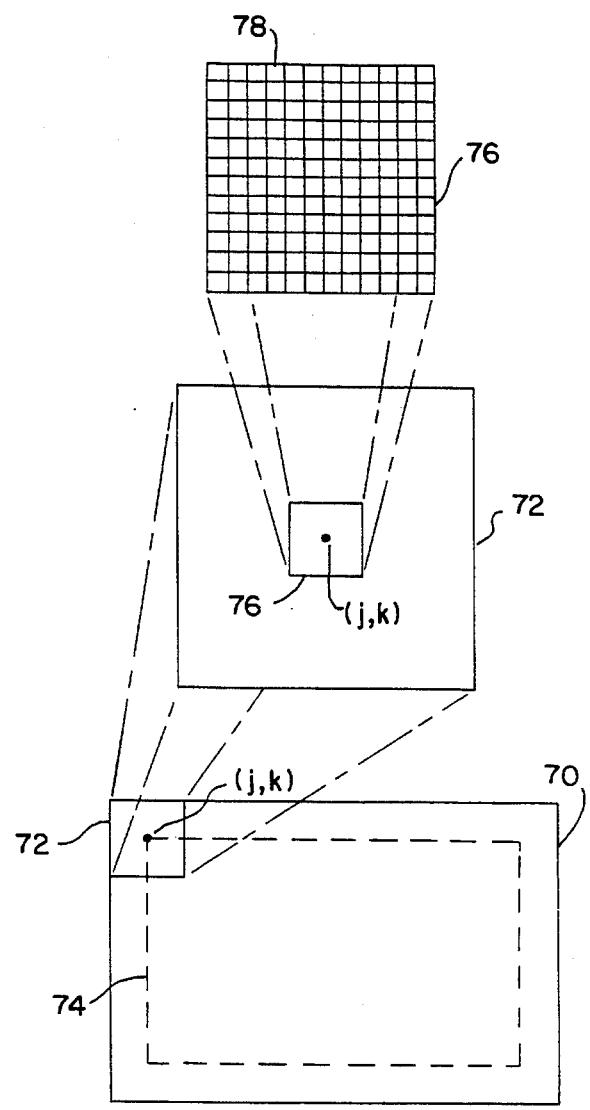
FIG. 7 is a series of illustrations of the areas and subareas of an image plane containing target lesions over which average pixel values are calculated for a defined pixel location (j,k).

The calculations of $S_{MB}$ and $\sigma_{MB}$ may be better explained with reference to FIG. 6. FIGS. 6 and 7 are not intended to represent scale drawings of any portion of an actual image plane, but are used for explanatory purposes only. A digitized background image plane 60 consists of a gray scale texture pattern of pixels containing no pixels representative of a lesion detection. Each pixel is represented by digital data stored in the analysis system 44. The analysis computer 44 first establishes an averaging area 62, which is large compared to the projected area of a target lesion, centered at the defined pixel coordinate (j,k) over which $\sigma_B$ will be calculated. The averaging area 62 is preferably a 1 cm² area. Note that, by this method, a 5 mm region on either side of the center coordinate is required for the calculation. This requirement cannot be met for pixel coordinates closer than 5 mm from the edge of the image 60. Therefore, pixel locations near the edge of the image 60, those pixels in FIG. 4 between the dashed line 64 and the edge of the image 60, will not be included in the calculation and will be considered undefined pixel locations. Within the large averaging area 62 a smaller sample size area 66 is defined. The smaller sample size area 66 is preferably a square area of side ⅔ times the target sphere diameter and consists of n pixels 68.

The analysis system computes two values as it proceeds. The first value is of the mean pixel value $S_{11}$ in the small sampling area 66. (The 11 subscript refers to the 1st row and 1st column in the matrix of sampling areas 66 in averaging area 62.) The second value is of $S_{11}^2$. For example, suppose the sampling area 66 consists of 12×12=144 pixels, as shown. Then:

$$S_{11} = \frac{1}{144} \sum_{i=1}^{144} P_i^m. \quad (7)$$

Preferably, $S_{11}$ corresponds to the mean of the "amplitude" pixel value. This corresponds to m=1 in Equation 3. Thus, $S_{11}$ is preferably just the mean pixel value. If pixel values are squared before summing, corresponding to m=2, $S_{11}$ would correspond to the mean of "intensity" pixel values. A method of Receiver Operator Characteristic (ROC) analysis using human observers may be used to optimize the m value which should be used to calibrate the automatic analysis results with human based evaluations of ultrasound scanner systems and configurations. However, whereas the choice of m may have some effect on detectability, it has been shown that detectability is only a weak function of m for $¼<m<2$.

After the values from $S_{11}$ and $S_{11}^2$ for sampling area 66 are found, the small sampling area 66 is shifted within the larger averaging area 62 and the next set of values, e.g., $S_{12}$ and $S_{12}^2$, are found. The shifted sampling areas 66 may overlap without greatly affecting the final result, even though such areas would not be completely independent. Thus, for example, 7×7=49 sampling areas 66, each 3 mm square, may be used in a single 1 cm averaging area 62. This process continues until all of the sampling area locations in the averaging area 62 have been addressed.

Note that it is not necessary to save in memory all values of $S_{pg}$ and $S_{pg}^2$ for each sampling area (p,g). Only the "ensemble" averages over the averaging area 62 need be saved. The "ensemble" average of $S_{pg}$ is $S_{MB}$ and the ensemble average of $S_{pg}^2$ may be defined as $T_B$. Thus, for defined pixel location (j,k):

$$S_{MB}(j,k) = \frac{1}{S} \sum_{p=1}^{\sqrt{s}} \sum_{q=1}^{\sqrt{s}} S_{pg} \tag{8}$$

and $$T_B(j,k) = \frac{1}{S} \sum_{p=1}^{\sqrt{s}} \sum_{q=1}^{\sqrt{s}} S_{pg}^2 \tag{9}$$

where s is the number of sampling areas 66 in the averaging are 62. Thus, in practice, $S_{MB}$ and $T_B$ may be achieved by accumulating sums of pixel values and squared pixel values throughout the averaging area 62. Note that for a 1 cm$^2$ averaging area 62 $S_{MB}$ is equivalent to at least 100 mm$^2$/9 mm$^2$, or approximately 11, independent ensemble element calculations for a 3 mm×3 mm lesion area. The standard deviation of the ensemble pixel value arranges $S_{pg}$ over the averaging area 62 may then be found as:

$$\sigma_B(j,k) = \sqrt{T_B(j,k) - S_{MB}^2(j,k)} \tag{10}$$

This procedure is then repeated for averaging areas centered at defined (j,k) coordinate pixel locations throughout the image background plane 60.

Note that since the standard deviation of the background texture will be generally consistent over areas approximately 1 cm$^2$, it is not necessary to calculate $\sigma_B$ at every (j,k) position. For example, $\sigma_B$ values may be calculated for averaging areas 62 centered 1 mm apart in the image plane 60. This will speed up the computation time with little effect on the analysis result. If values for less than all (j,k) positions are calculated, the values from the averaging area which includes, and has the closest (j,k) center coordinate to, the (j,k) pixel coordinate of interest will be used in calculating the final SNR value. Moreover, $\sigma_B$ may be calculated using corresponding (j,k) coordinate centered averaging areas from multiple independent background image planes, which would be parallel to each other in the imaging phantom. As mentioned above, this will result in better $\sigma_B$ estimates.

As has already been mentioned, in the preferred automated system of the present invention, $S_{MB}$ is calculated over a target plane image rather than the background plane image. Thus, the $S_{MB}$ (j,k) values calculated as described above are preferably only used to calculate $\sigma_B$ (j,k). To calculate the $S_{MB}$ value which will be used in evaluating Equation 6, the above procedure is repeated for the calculation of $S_{MB}$ (j,k) values with the image plane 60 being the target plane image rather than the background plane image.

Calculation of the lesion pixel value average $S_L$ for a pixel at coordinate (j,k) is described in more detail with respect to FIG. 7. In this case, the digitized image from which the calculation is made is an image plane 70 which is centered on the plane in the imaging phantom which contains target lesions. The area 72 in the lesion plane 70 is centered at coordinates (j,k) and corresponds to the averaging area 62 in a parallel background plane, 60 in FIG. 6. As was discussed above, pixels having coordinates close to the edge of the image plane 70, e.g., outside of the dashed line 74, are not defined or used for the calculation. At the center of the area 72, a smaller sampling area 76 centered on the pixel at coordinate (j,k) is defined. The sampling size area 76 is preferably a square area of side ⅔ times the diameter of the target sphere in the lesion plane under examination 70. This area may contain, for example, 12×12=144 pixels 78. The lesion plane average pixel value for the pixel at location (j,k) is then simply calculated as, for example, the sum of the pixel data values of the pixels 78 in the sample size area 76, divided by the number of pixels 78 in the sample size area 76.

Figure 8:
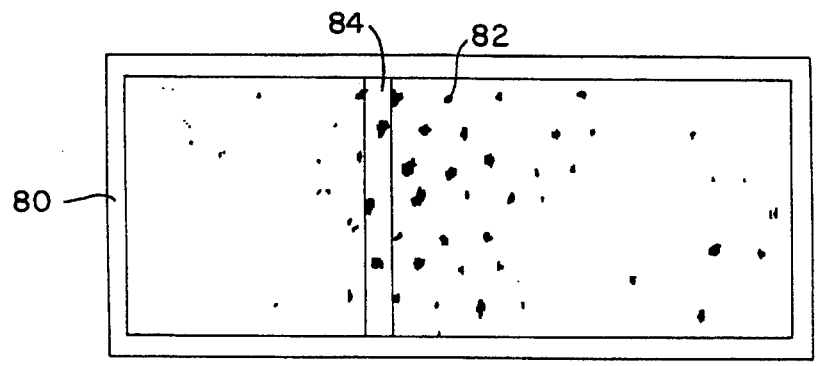
FIG. 8 is an illustrated example map of pixel locations having an $(SNR)_L$ less than a threshold value of −2, resulting from an image of a phantom plane containing 4 millimeter diameter target lesions with −15 db contrast for which the SNR of each location has been calculated in accordance with the present invention.
Figure 10:
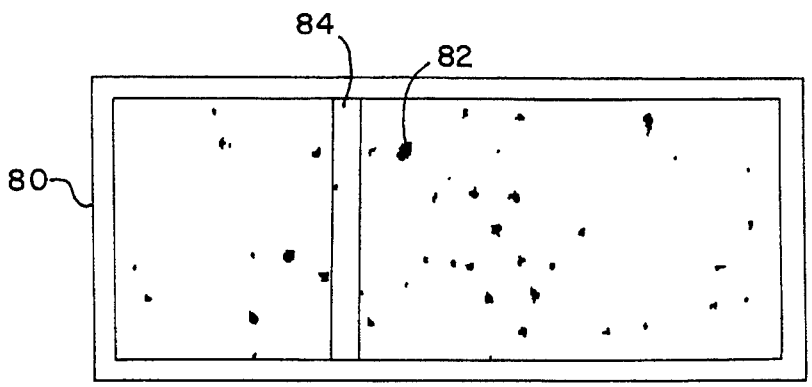
FIG. 10 is an illustrative example map of pixel locations having an $(SNR)_L$ greater than a threshold value of +2, resulting from an image of a phantom plane containing 4 millimeter diameter target lesions having a contrast of +3 dB for which the $(SNR)_L$ of each location has been calculated in accordance with the present invention.

Having determined $S_L$, $S_{MB}$, and $\sigma_B$, the signal to noise ratio $(SNR)_L$ may be calculated for each defined pixel location in the image plane 70 using equation 6. Maps of pixel positions, (j,k), having signal to noise ratios surpassing a first threshold value may be plotted and displayed. FIG. 8 shows an example of a map of pixel locations where (SNR) surpasses the first threshold using the above described calculation as applied to a 3.5 MHz linear array scan, using an Acuson L382 scanner, of a phantom section containing 4 mm diameter target lesion spheres made of a material having a −15 db contrast with respect to the background material. Similarly, FIG. 10 shows an example of a map of pixel locations having SNR) values surpassing the first threshold using calculations as described above from the digitized image of a 3.5 MHz linear array scan, also using the Acuson L382 scanner, of a phantom section containing 4 mm diameter target spheres made of material having +3 db contrast with respect to the background material. The focus depth for both scans was set at 7 cm.

The first threshold value used for the FIG. 8 map was −2.0 and the first threshold value used for the FIG. 10 map was +2.0. The thresholds (−2.0 or +2.0) were chosen after making many comparisons between such depictions as shown in FIG. 8 and FIG. 10 and human observer impressions for ultrasound images of multiple combinations of lesion diameter and contrasts of the target spheres in imaging phantoms. In each map, those (j,k) coordinates having a calculated absolute value $|(SNR)_L| \geq 2.0$ are represented by a black dot. The dark border of the two maps indicates pixel coordinates which are undefined and not used in the calculation. Note that pseudo lesion images 82 may appear in the mapping.

Figure 9:
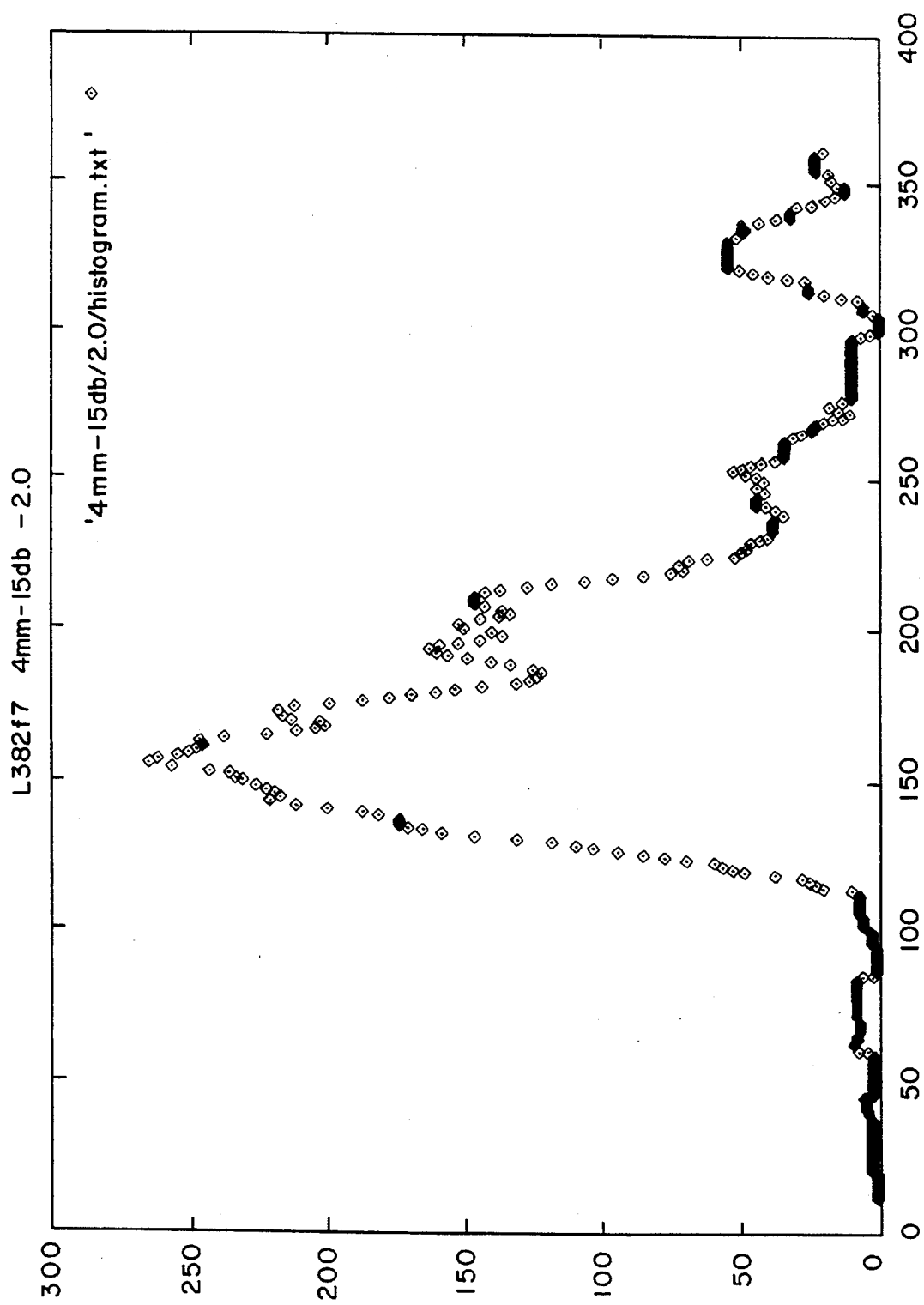
FIG. 9 is a histogram corresponding to the map of FIG. 8 showing the number of pixel locations within a series of 1 centimeter depth ranges which are more negative than the threshold value, and which is used to determine the proximal and distal depth range resolution of an ultrasound scanner.
Figure 11:
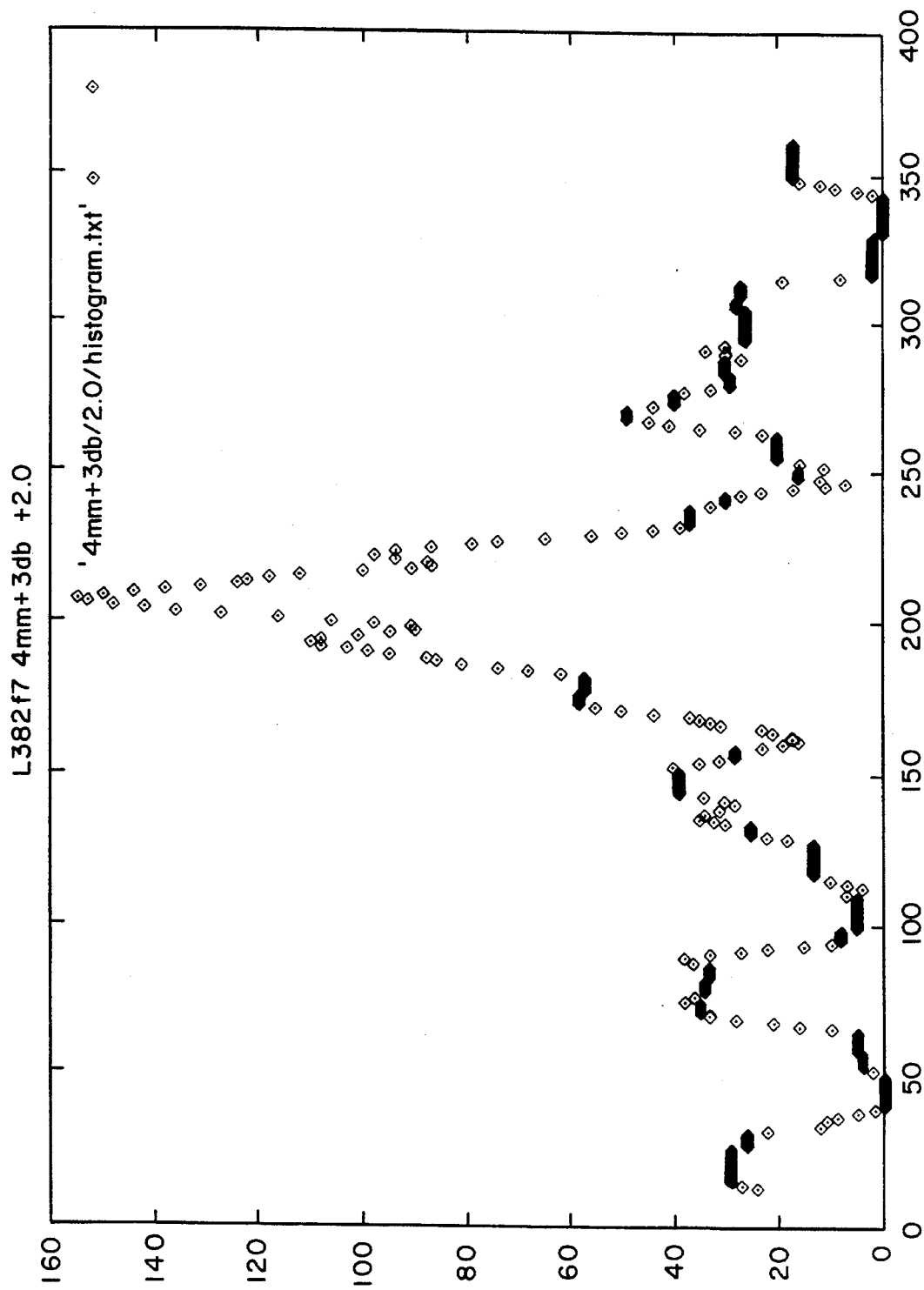
FIG. 11 is a histogram corresponding to the map of FIG. 10 showing the number of pixel locations within a series of 1 centimeter depth ranges which exceed the threshold value, and which is used to determine the proximal and distal depth range limits of resolution of an ultrasound scanner.

FIGS. 9 and 11 are histograms of the number of pixel locations with $(SNR)_L$ values beyond the first threshold value in a 1 cm depth range of the image, versus axial pixel coordinate, for the mappings of FIGS. 8 and 10 respectively. Examples of 1 cm depth areas, over which pixel values surpassing the first threshold are summed in generation of the histograms, are shown at 84, not to scale, in FIGS. 2, 8, and 10.

A second threshold level may preferably be established whereby the histogram data may be used to determine the proximal and distal depth range limits of detectability. Again, this second threshold value may be chosen to optimize agreement with averaged proximal and distal depth range values for human observers. The threshold pixel number per 1 cm depth interval 84 may be taken to be half of the number of pixels contained in the projected area of 1 target lesion. For the 4 mm diameter lesions of FIGS. 8–11, this number is 40 pixels. Thus, using the fact that in this example there are 25 pixels per centimeter, the proximal depth where resolution begins was found to be approximately 4.8 cm, and the distal depth at which resolution disappears was found to be approximately 14.3 cm for the 4 mm, −15 dB case shown in FIG. 9. Similarly, proximal depth of 6.1 cm and a distal depth range of 11.1 cm was found for the 4 mm, +3 dB case shown in FIG. 11.

Tables 1 and 2 show values of proximal and distal depth range limits for three experienced human observers of ultrasound images, and corresponding values for the automated analysis just described for images made using the Acuson 3.5 MHz L382 scan head focused at 7 cm for lesions of various diameters and contrasts. Dashes in the tables indicate no detections at any depth.

TABLE 1

Proximal Limit of Detectability (cm.)
(Acuson 3.5 MHz L382 array focused at 7 cm.)

| | Lesion Type | | | | |
|---|---|---|---|---|---|
| | 4 mm −15 dB | 4 mm −9 dB | 4 mm +3 dB | 3 mm −15 dB | 3 mm +3 dB |
| Obs. A | 5.5 | 6.0 | 7.0 | 6.5 | 6.5 |
| Obs. B | 5.0 | 5.5 | 7.5 | 6.0 | — |
| Obs. C | 5.7 | 6.0 | 7.0 | 6.0 | — |
| Auto. System | 4.8 | 5.2 | 6.1 | 6.4 | 5.7 |

TABLE 2

Distal Limit of Detectability (cm.)
(Acuson 3.5 MHz L382 array focused at 7 cm.)

| | Lesion Type | | | | |
|---|---|---|---|---|---|
| | 4 mm −15 dB | 4 mm −9 dB | 4 mm +3 dB | 3 mm −15 dB | 3 mm +3 dB |
| Obs. A | 11.0 | 11.5 | 10.0 | 7.5 | 7.5 |
| Obs. B | 11.0 | 12.0 | 9.5 | 8.0 | — |
| Obs. C | 11.0 | 11.0 | 11.0 | 8.0 | — |
| Auto. System | 13.3 | 10.7 | 11.1 | 7.2 | 6.6 |

(For 4 mm, −6 dB, 3 mm, −9 dB, and 3 mm, −6 dB no lesions were detected by observers or the automated system.)

Tables 3 and 4 show similar results for the proximal and distal depth range limits of detectability for the automated analysis system and human observers for images of target lesions of varying diameters and contrasts using an Acuson 5 MHz L558 linear array focused at the 5 cm depth range.

TABLE 3

Proximal Limit of Detectability
(Acuson 5 MHz L558 array focused at 5 cm.)

| | Lesion Type | | | | | | |
|---|---|---|---|---|---|---|---|
| | 4 mm −15 dB | 4 mm −9 dB | 4 mm −6 dB | 4 mm +3 dB | 3 mm −15 dB | 3 mm −9 dB | 3 mm +3 dB |
| Obs. A | 1.1 | 0.6 | 1.8 | 0.5 | 1.7 | 2.4 | 1.7 |
| Obs. B | 1.2 | 0.7 | 1.2 | 2.4 | 1.7 | 3.1 | 3.5 |
| Obs. C | 1.2 | 0.5 | 3.6 | 2.6 | 1.9 | 3.1 | 4.4 |
| Auto. | 0.5 | 0.5 | 0.9 | 0.7 | 0.8 | 1.5 | 1.1 |

TABLE 4

Distal Limit of Detectability (cm.)
(Acuson 5 MHz L558 array focused at 5 cm.)

| | 4 mm −15 dB | 4 mm −9 dB | 4 mm −6 dB | 4 mm +3 dB | 3 mm −15 dB | 3 mm −9 dB | 3 mm +3 dB |
|---|---|---|---|---|---|---|---|
| Obs. A | 7.3 | 7.4 | 6.0 | 6.8 | 6.2 | 5.6 | 5.2 |
| Obs. B | 9.0 | 8.4 | 6.5 | 6.3 | 5.3 | 5.7 | 4.9 |
| Obs. C | 8.6 | 7.7 | 5.6 | 6.5 | 5.5 | 5.5 | 7.4 |
| Auto. | 7.0 | 7.3 | 5.5 | 6.1 | 4.4 | 3.5 | 5.0 |

(No 3 mm, −6 dB lesions were detected by observers or the automated system.)

As can be seen from these tables, agreement between the automated analysis system and human observers is, overall, rather good. Automated system values of both the proximal and distal depth limits tend to be smaller than those of the human observers. From a large body of results, calculated using many different target diameters and contrasts, a numerical "merit value" may be computed at any depth. Such a figure of merit may be based on the sum of the inverse of the diameters of detectable lesions at a given depth. For example, the merit value from the automated assessment for a 6–8 cm depth range may be set equal to the sum of the inverses of the diameters of simulated focal lesions detectable at 7 cm depth for all diameters and contrasts considered.

Modifications to the automated system may be made which address the possibility that false positives, i.e., interpretation of pixel value fluctuation extrema by the system as being in the lesion detection area when, in actuality, they are not, may result in unreasonably small proximal detection limits or large distal detection limits. One method for addressing this possibility is to require that a continuous set of pixel locations in which the value of $SNR_L$ has surpassed the first threshold level must contain at least ¼ or ⅓ of the number of pixels corresponding to the projected area of the searched for target lesion. In other words, for a 4 mm target lesion corresponding to 200 pixels, a continuous set of at least 25 pixel locations surpassing the first threshold level would be required for the locations to be included in the number of locations over the threshold in a centimeter depth range for the final calculation of the proximal and distal limits of detectability. A second modification is to require that, in order for the total number of pixel locations exceeding the first threshold in a 1 cm depth range to be counted in determining the proximal and distal limits of the resolution zone, there must be a minimum number of continuous first threshold regions as described in the beginning of this paragraph contributing in that 1 cm depth range. This minimum number might be 2 or 3. Setting this number greater than 1 helps to eliminate fluke false positives since each 1 cm depth increment should contain several, and preferably at least 7, isolated simulated target lesions.

The computer analysis of the digitized image data may be refined to account for any type of scan head, e.g., sector, curved linear array or other types of arrays, etc. Images made with linear arrays tend to have significant uncontrollable lateral variations in local mean pixel value. As described above, the standard deviation for the lesion area mean is preferably computed over a 1 $cm^2$ square area containing each pixel which is at least 0.5 cm from the image boundary. The normal standard deviation calculation assumes that there is no significant variation in the local pixel mean over the 1 $cm^2$ area. When variation of the mean is significant, a common occurrence near edges of the image, the normally computed standard deviations, which assume a single mean, are erroneously high. Such a high value results in a smaller value of SNR than is reasonable; i.e., detectability is falsely decreased whether a lesion has a positive or negative contrast. To solve the problem, a 2-D surface fit (corresponding to a curve fit in 1-D) may be programmed over the 1 $cm^2$ averaging area and the standard deviation may be calculated as a standard error of the estimate. The standard error of the estimate quantifies deviations from the fitted surface. If the surface corresponds to a constant mean pixel value, then the standard error of the estimate equals the normally calculated standard deviation.

The following is an exemplary program from the computer analysis system 44 to carry out the resolution analysis of ultrasound scanners as described above.

```
/* Program: allcontrast.c
   Author: Jason J. Rownd
   Date:   26 Sept 1994, extensive comments added 22 Aug 1994
   Revision: 28 Nov 1994
           generalized coordinates and pixels AND handles both
           positive and negative contrasts AND mean sigma or sigma
   Revision: 20Jan95
           rewrote histogram option to more correctly reflect depth profiles No part of this program may be used without the express written consent
   of the author.
*/

/* This program will use a simplified method to calculate sigma, as in the
   original contrast program.  The major difference is that we will be
   keeping track of the image location for background avg's and sigma's,
   including row AND column information. NOW using mean.dat for sigma.
*/
/* IMPORTANT apparently C does not like to have reference values less than
   zero when using array created using malloc.
*/
/* Revamped newcontrast.c to use notation developed 12Jul94
*/
/* some numbers to keep in mind when using this program are the number of
   pixels per mm for each image. most are 4 pixels/mm */
/****************************************************************************/
/* This program allows the user to specify the number of pixels per mm as  */
/* an input variable.  Subsequent values are computed from this information*/
/* However, to change these key values, the program must be edited and then*/
/* recompiled.  The key parameters, are for now, the large integration area*/
/* which is referred to as AA_?, or "averaging area", the step size that   */
/* this large area is moved, usually referred to a the grid or AA_step, the*/
/* smaller integration area which is referred to SS_?, or 'sample size',   */
/* and finally the step size of the movement of the SS area.  For now, the */
/* areas are treated as exact squares.  In the future, we may change this  */
/* to more accurately reflect the size and shape of the target lesions in  */
/* our images.                                                             */
/****************************************************************************/ include <stdio.h>
include <string.h>
include <math.h> define INPUT_PARAM_FILE_NAME "input1.dat"      /*contains all required
                                                  program parameters*/
#define TARGET_FILE_NAME "target.pnm"           /*lesion containing image*/
#define BACKGROUND_FILE_NAME "background.pnm"   /*no lesions in this image*/
#define SIGMA_FILE_NAME "sigma.dat"             /*output file to contain
                                                  the numerical values of
                                                  sigma at the grid points*/
#define MEAN_SIGMA_FILE_NAME "mean.dat"         /*previously derived values*/
#define OUTPUT1_FILE_NAME "output1.txt"         /*output file to contain the
                                                  numerical values of SNR1
                                                  for all pixel locations*/
#define HISTOGRAM_FILE_NAME "histogram.txt"     /*output file of histogram*/
#define CONTRAST_FILE_NAME "contrast.pnm"       /*0-255 greyscale image of
                                                  the SNR1 values*/
#define CONTRAST_BW_FILE_NAME "contrast_bw.pnm" /*0 and 255 greyscale image
                                                  (black and white) of those
                                                  pixel locations that fall
                                                  below threshold set by user*/
#define I_BAR_FILE_NAME "i_bar.pnm"             /*greyscale image of Ibar*/
#define SIGMA_IMAGE_FILE_NAME "sigma_image.pnm" /*greyscale image of sigma*/
#define MEAN_SIGMA_IMAGE_FILE_NAME "mean_sigma_image.pnm"
#define I_FILE_NAME "i.pnm"                     /*greyscale image of I*/
```

```c
#define AA_diam_mm 10.0   /* defines averaging area diameter in mm */
#define AA_step_mm 1.0    /* defines averaging area shift in mm */
/*#define SS_diam_mm 3.0 defines sample size diameter in mm -4mm target */
/* defined in input1.dat */
#define SS_step_mm 1.0    /* defines sample size shift in mm */
define histo_size_mm 10.0 /* defines depth of histogram averaging */ define zed 0    /* define a zero parameter, just in case */ main () { /* the beginning of the program */ unsigned char **background_data_ptr;   /* the background image data */
    unsigned char **target_data_ptr;       /* the target image data */ float **background_avg_ptr;   /* to store <avg> of all 15x15
                                     areas inside 40x40 */
    float **target_avg_ptr;       /* to store avg of 15x15 area */
    float **background_avg_2_ptr; /* to store <avg**2> of all 15x15 ... */
    float **sigma_ptr;            /* to store sigma from background 15x15's
                                     inside 40x040 */
    float **mean_sigma_ptr;       /* previously derived values */
    float **contrast_ptr;         /* contrast results */
    float **target_two_ptr;       /* extra array to hold target avg used in
                                     place of background avg for SNR */

FILE *background_file;     /* background image file */
    FILE *target_file;         /* target image file */
    FILE *sigma_file;          /* sigma results file */
    FILE *mean_sigma_file;     /* previously derived values */
    FILE *output1_file;        /* misc output file */
    FILE *histogram_file;      /* misc output file */
    FILE *contrast_file;       /* misc image file */
    FILE *contrast_bw_file;    /* misc image file */
    FILE *i_bar_file;          /* misc image file */
    FILE *sigma_image_file;    /* misc image file */
    FILE *i_file;              /* misc image file */
    FILE *mean_sigma_image_file;
    FILE *input_param_file;    /* input parameters */ int ch,i,j,k,l,m,n;        /* looping variables and character check */
    int ij_count,kl_count,mn_count; /* tracking number of loops used */
    int ig,jg;                 /* looping variables in grid layout */
    int row_index;             /* looping variable, exact pixel location */
    int col_index;             /* looping variable, exact pixel location */
    int row_k,col_l;           /* conversion of looping variable into grid coor.*/
    int row,column;            /* defining number of rows and columns in image */
    int pixel_max;             /* defining max possible greyscale in images */
    int AA_rad,AA_step;        /* set values for averaging area */
    int SS_rad,SS_step;        /* set values for sample size */
    int histo_size;            /* set value of histogram avg'ing size */
    int row_temp,col_temp;     /* temporary variables, used at will */
    int line_max,tmp1,tmp2;
    int ig_start,jg_start;     /* start values for grid, see row_k */
    int positive;              /* =1 for positive contrast, =0 for negative */
    int mean_use;              /* =1 for case using mean of multiple sigmas */
    int scale_increment;       /* counts loops in top and bottom sections of
                                  histogram */ char line[100];   /* string variable used to read in data from image file */ float temp_sum;            /* temporary variable, used at will */
    float temp_sum_2;          /* temporary variable, used at will */
    float target_sum;          /* temp. variable used to track summation */
    float sigma_temp;          /* temp. variable used to insure float assignment */
    float con_min,con_max;     /* min and max of SNR1 values */
    float thresh;              /* user defined threshold value */
```

```c
    float pixel_per_mm;     /* entered value for pixels per mm in image */
    float tmpmean;
    float SS_diam_mm;       /* read from INPUT_PARAM... */
    float scale_factor;     /* used with histogram top and bottom sections */ unsigned char temp_char;  /* temp variable used in stripping the header
                                 from the image files */
    unsigned char mean_temp_char;
/**************************************************************************/
/* obtaining user defined information and performing the necessary conver- */
/* sions from real space values to pixel values                            */
/**************************************************************************/
    input_param_file = fopen(INPUT_PARAM_FILE_NAME, "r");
    if (input_param_file == NULL) {
        (void) printf("Can not open %s\n",INPUT_PARAM_FILE_NAME);
    }

(void) fgets(line, sizeof(line), input_param_file);
    line[strlen(line)-1]='\0';
    (void) sscanf(line, "%d", &positive);

(void) fgets(line, sizeof(line), input_param_file);
    line[strlen(line)-1]='\0';
    (void) sscanf(line, "%f", &pixel_per_mm);

(void) fgets(line, sizeof(line), input_param_file);
    line[strlen(line)-1]='\0';
    (void) sscanf(line, "%d", &mean_use);

(void) fgets(line, sizeof(line), input_param_file);
    line[strlen(line)-1]='\0';
    (void) sscanf(line, "%d", &line_max);

(void) fgets(line, sizeof(line), input_param_file);
    line[strlen(line)-1]='\0';
    (void) sscanf(line, "%f", &thresh);

(void) fgets(line, sizeof(line), input_param_file);
    line[strlen(line)-1]='\0';
    (void) sscanf(line, "%f", &SS_diam_mm);

AA_rad  = (int)(AA_diam_mm*pixel_per_mm/2.0);
    AA_step = (int)(AA_step_mm*pixel_per_mm);
    SS_rad  = (int)(SS_diam_mm*pixel_per_mm/2.0);
    SS_step = (int)(SS_step_mm*pixel_per_mm);
    histo_size = (int)(histo_size_mm*pixel_per_mm);

(void) printf("Some values used in this program as a result of this \n");
    (void) printf("number are listed below, CTRL C at any time if wrong.\n");
    (void) printf("AA_rad = %d, AA_step = %d, SS_rad = %d, SS_step = %d\n",
              AA_rad,AA_step,SS_rad,SS_step);
    (void) printf("histo_size = %d, pixel_per_mm = %f\n",
              histo_size,pixel_per_mm);

/**************************************************************************/
/* This section will open all the necessary files that are used in the rest */
/* of the program.  There is no math present here.                          */
/**************************************************************************/ background_file = fopen(BACKGROUND_FILE_NAME, "r");
    if (background_file == NULL) {
        (void) printf("Can not open %s\n",BACKGROUND_FILE_NAME);
    } target_file = fopen(TARGET_FILE_NAME, "r");
```

```c
    if (target_file == NULL) {
        (void) printf("Can not open %s\n", TARGET_FILE_NAME);
    } sigma_file = fopen(SIGMA_FILE_NAME, "w");
    if (sigma_file == NULL) {
        (void) printf("Can not open %s\n", SIGMA_FILE_NAME);
    } mean_sigma_file = fopen(MEAN_SIGMA_FILE_NAME, "r");
    if (mean_sigma_file == NULL) {
        (void) printf("Can not open %s\n", MEAN_SIGMA_FILE_NAME);
    } output1_file = fopen(OUTPUT1_FILE_NAME, "w");
    if (output1_file == NULL) {
        (void) printf("Can not open %s\n",OUTPUT1_FILE_NAME);
    } histogram_file = fopen(HISTOGRAM_FILE_NAME, "w");
    if (histogram_file == NULL) {
        (void) printf("Can not open %s\n",HISTOGRAM_FILE_NAME);
    } i_bar_file = fopen(I_BAR_FILE_NAME, "w");
    if (i_bar_file == NULL) {
        (void) printf("Can not open %s\n",I_BAR_FILE_NAME);
    } sigma_image_file = fopen(SIGMA_IMAGE_FILE_NAME, "w");
    if (sigma_image_file == NULL) {
        (void) printf("Can not open %s\n",SIGMA_IMAGE_FILE_NAME);
    } mean_sigma_image_file = fopen(MEAN_SIGMA_IMAGE_FILE_NAME, "w");
    if (mean_sigma_image_file == NULL) {
        (void) printf("Can not open %s\n",MEAN_SIGMA_IMAGE_FILE_NAME);
    } i_file = fopen(I_FILE_NAME, "w");
    if (i_file == NULL) {
        (void) printf("Can not open %s\n",I_FILE_NAME);
    }

/****************************************************************************/
/* Once the files are open we can read the information from them. In part-  */
/* icular, the row, column, and pixel_max values found the three line       */
/* header at the top of each portable bitmap image file.                    */
/****************************************************************************/
    (void) fgets(line, sizeof(line), background_file);
    line[strlen(line)-1] = '\0';
    (void) fgets(line, sizeof(line), background_file);
    line[strlen(line)-1] = '\0';
    (void) sscanf(line, "%d %d", &column, &row);
    (void) printf("row=%d  column=%d\n",row,column);
    (void) fgets(line, sizeof(line), background_file);
    line[strlen(line)-1] = '\0';
    (void) sscanf(line, "%d", &pixel_max);

(void) fgets(line, sizeof(line), target_file);
    line[strlen(line)-1] = '\0';
    (void) fgets(line, sizeof(line), target_file);
    line[strlen(line)-1] = '\0';
    (void) sscanf(line, "%d %d", &column, &row);
```

```
   (void) printf("row=%d  column=%d\n",row,column);
   (void) fgets(line, sizeof(line), target_file);
   line[strlen(line)-1] = '\0';
   (void) sscanf(line, "%d", &pixel_max);

/****************************************************************************/
/* Time to allocate memory for and fill the arrays for background and       */
/* target and any other pointers.  These pointers are set up with row and   */
/* column designations, along with a character type. i.e. unsigned char,    */
/* float or whatever.  Once you use the full designation of row and column  */
/* indexing, these pointers are considered fully dereferenced and may be    */
/* exactly like a normal two-dimensional array.  An error check follows     */
/* each allocation to insure that there is enough memory to handle the size*/
/* of the pointer structure.                                                */
/****************************************************************************/ background_data_ptr = (unsigned char **) malloc(sizeof(char*)*row);
   if (background_data_ptr == NULL) {
      (void) printf("Can not allocate memory for rows...\n");
      exit(8);
   }
   for (i=0;i<row;i++) {
      background_data_ptr[i] = (unsigned char *) malloc(sizeof(char)*column);
      if (background_data_ptr[i] == NULL) {
         (void) printf("Can not allocate background_data_ptr[%d]\n",i);
         exit(9);
      }
      fread(background_data_ptr[i], sizeof(char), column, background_file);
   } target_data_ptr = (unsigned char **) malloc(sizeof(char*)*row);
   if (target_data_ptr == NULL) {
      (void) printf("Can not allocate memory for rows...\n");
      exit(8);
   }
   for (i=0;i<row;i++) {
      target_data_ptr[i] = (unsigned char *) malloc(sizeof(char)*column);
      if (target_data_ptr[i] == NULL) {
         (void) printf("Can not allocate background_data_ptr[%d]\n",i);
         exit(8);
      }
      fread(target_data_ptr[i], sizeof(char), column, target_file);
   }

(void) printf("The image files have been read into memory.\n");
   (void) printf("Allocating memory for remaing arrays.\n");

background_avg_ptr = (float **) malloc(sizeof(float *)*row);
   if (background_avg_ptr == NULL) {
      (void) printf("Can not allocate rows for background_avg_ptr\n");
      exit(8);
   }
   for (i=0;i<row;i++) {
      background_avg_ptr[i] = (float *) malloc(sizeof(float)*column);
      if (background_avg_ptr[i] == NULL) {
         (void) printf("Can not allocate background_avg_ptr[%d]\n",i);
         exit(8);
      }
   } target_avg_ptr = (float **) malloc(sizeof(float *)*row);
   if (target_avg_ptr == NULL) {
      (void) printf("Can not allocate rows for target_avg_ptr\n");
      exit(8);
   }
```

```c
for (i=0;i<row;i++) {
    target_avg_ptr[i] = (float *) malloc(sizeof(float)*column);
    if (target_avg_ptr[i] == NULL) {
        (void) printf("Can not allocate target_avg_ptr[%d]\n",i);
        exit(8);
    }
} target_two_ptr = (float **) malloc(sizeof(float *)*row);
if (target_two_ptr == NULL) {
    (void) printf("Can not allocate rows for target_two_ptr\n");
    exit(8);
}
for (i=0;i<row;i++) {
    target_two_ptr[i] = (float *) malloc(sizeof(float)*column);
    if (target_avg_ptr[i] == NULL) {
        (void) printf("Can not allocate target_two_ptr[%d]\n",i);
        exit(8);
    }
} background_avg_2_ptr = (float **) malloc(sizeof(float *)*row);
if (background_avg_2_ptr == NULL) {
    (void) printf("Can not allocate rows for background_avg_2_ptr\n");
    exit(8);
}
for (i=0;i<row;i++) {
    background_avg_2_ptr[i] = (float *) malloc(sizeof(float)*column);
    if (background_avg_2_ptr[i] == NULL) {
        (void) printf("Can not allocate background_avg_2_ptr[%d]\n",i);
        exit(8);
    }
} sigma_ptr = (float **) malloc(sizeof(float *)*row);
if (sigma_ptr == NULL) {
    (void) printf("Can not allocate rows for sigma_ptr\n");
    exit(8);
}
for (i=0;i<row;i++) {
    sigma_ptr[i] = (float *) malloc(sizeof(float)*column);
    if (sigma_ptr[i] == NULL) {
        (void) printf("Can not allocate sigma_ptr[%d]\n",i);
        exit(8);
    }
} mean_sigma_ptr = (float **) malloc(sizeof(float *)*row);
if (mean_sigma_ptr == NULL) {
    (void) printf("Can not allocate rows for mean_sigma_ptr\n");
    exit(8);
} for (i=0;i<row;i++) {
    mean_sigma_ptr[i] = (float *) malloc(sizeof(float)*column);
    if (mean_sigma_ptr[i] == NULL) {
        (void) printf("Can not allocate mean_sigma_ptr[%d]\n",i);
        exit(8);
    }
} contrast_ptr = (float **) malloc(sizeof(float *)*row);
if (contrast_ptr == NULL) {
    (void) printf("Can not allocate rows for contrast_ptr\n");
    exit(8);
}
```

```c
    for (i=0;i<row;i++) {
        contrast_ptr[i] = (float *) malloc(sizeof(float)*column);
        if (contrast_ptr[i] == NULL) {
            (void) printf("Can not allocate contrast_ptr[%d]\n",i);
            exit(8);
        }
    }

(void) printf("Allocations successfully completed.\n");

/****************************************************************************/
/* NOW, we begin the first part of our calculations. This section will      */
/* find the pixel averages in the sample size, then find the standard dev-  */
/* iation of a subset of all such sample size results for a given averaging */
/* area centered at a particular set of grid coordinates. The large aver-   */
/* aging area is then shifted by AA_step and the process is repeated. The   */
/* limits on the for loops are determined by the image size and the sizes   */
/* the small sample size area and the larger averaging area. Additionally,  */
/* the subset of locations used to find the standard deviation are those    */
/* locations that are 1mm apart. This can be changed with a "simple" revi-  */
/* sion of the computer code. For now, I am using AA_step to control the    */
/* motion of the larger AA_? area and SS_step to control the motion the     */
/* smaller SS_? inside the AA_? area.                                       */
/*                                                                          */
/* We use the background image to find value of the standard deviation,     */
/* sigma.                                                                   */
/****************************************************************************/

(void) printf("Beginning the background calculations...\n");

/*** Defining limits and motion of the large averaging area, AA_? ***/ ig_start = (int)(pixel_per_mm)*(int)((AA_rad+(int)(pixel_per_mm/2))/
               (int)pixel_per_mm);
    jg_start = (int)(pixel_per_mm)*(int)((AA_rad+(int)(pixel_per_mm/2))/
               (int)pixel_per_mm);

for (ig=ig_start;ig<=row-1-AA_rad;ig=ig+AA_step) {
        for (jg=jg_start;jg<=column-1-AA_rad;jg=jg+AA_step) {
            background_avg_ptr[ig][jg]=0.0;
            background_avg_2_ptr[ig][jg]=0.0;
            kl_count = 0;

/***** Defining limits and motion of the small sample size area SS_? *****/
            for (k=ig-(AA_rad-SS_rad);k<=ig+(AA_rad-SS_rad);k=k+SS_step) {
                for (l=jg-(AA_rad-SS_rad);l<=jg+(AA_rad-SS_rad);l=l+SS_step) {
                    temp_sum = 0.0;
                    mn_count = 0;

/***** Defining the size of the small sample size area *****/
                    for (m=k-SS_rad;m<=k+SS_rad;m=m+1) {
                        for (n=l-SS_rad;n<=l+SS_rad;n=n+1) {
                            temp_sum = temp_sum + background_data_ptr[m][n];
                            mn_count=mn_count+1;
                        }
                    }
                    background_avg_ptr[ig][jg]=background_avg_ptr[ig][jg]+temp_sum;
                    background_avg_2_ptr[ig][jg]=background_avg_2_ptr[ig][jg]+
                                                 (temp_sum*temp_sum);
                    kl_count=kl_count+1;

}
            } /* end the k and l loops at a given ig,jg coordinate */

/***** correctly scaling the averages needed to get sigma *****/
            background_avg_ptr[ig][jg]=background_avg_ptr[ig][jg]/
```

```c
                                               (float)(kl_count*mn_count);
         background_avg_2_ptr[ig][jg]=background_avg_2_ptr[ig][jg]/
                                         (float)(kl_count*mn_count*mn_count);

/***** shortcut used to compute sigma, the standard deviation *****/
         sigma_ptr[ig][jg] = sqrt(background_avg_2_ptr[ig][jg]-
                    (background_avg_ptr[ig][jg]*background_avg_ptr[ig][jg]));
         }
      } /* end the ik,jl loop for 'position' coordinates */

/****************************************************************************/
/* Remember, we are using the target image to find both "I bar" and "I"    */
/****************************************************************************/

(void) printf("Beginning the target calculations...\n");

/***** defining centers of "I bar", all pixel locations *****/
     for (i=AA_rad;i<=row-1-AA_rad;i=i+1) {
        for (j=AA_rad;j<=column-1-AA_rad;j=j+1) {
           target_two_ptr[i][j]=0.0;
           kl_count = 0;

/***** defining size of area used to compute "I bar", AA_? *****/
           for (k=i-AA_rad;k<=i+AA_rad;k=k+1) {
              for (l=j-AA_rad;l<=j+AA_rad;l=l+1) {
                 target_two_ptr[i][j] = target_two_ptr[i][j] +
                                          target_data_ptr[k][l];
                 kl_count = kl_count +1;
              }
           }
           target_two_ptr[i][j] = target_two_ptr[i][j]/(float)(kl_count);
        }
     }

/***** defining centers of "I", all pixel locations *****/
     for (row_index=AA_rad;row_index<=row-1-AA_rad;row_index=row_index+1) {
        for (col_index=AA_rad;col_index<=column-1-AA_rad;col_index=col_index+1) {
           temp_sum=0.0;
           ij_count=0;

/***** defining size of area used to compute "I", SS_? *****/
           for (i=row_index-SS_rad;i<=row_index+SS_rad;i=i+1) {
              for (j=col_index-SS_rad;j<=col_index+SS_rad;j=j+1) {
                 temp_sum = temp_sum + target_data_ptr[i][j];
                 ij_count=ij_count+1;
              }
           }
           target_avg_ptr[row_index][col_index]=(float)(temp_sum)/
                                                 (float)(ij_count);

} /* end col_index loop */
     } /* end row_index loop */

/****************************************************************************/
     if (mean_use == 1) { for (i=0;i<row;i++) {
           for (j=0;j<column;j++) {
              mean_sigma_ptr[i][j]=0.0;
           }
        }

(void) printf("Reading mean.dat into mean_sigma_ptr\n");
        ij_count=0;
        while(1) {
           (void) fgets(line, sizeof(line), mean_sigma_file);
```

```
            line[strlen(line)-1]='\0';
            (void) sscanf(line,"%d %d %f",&tmp1,&tmp2,&tmpmean);
            if (tmp1 == 999)
                break;
            mean_sigma_ptr[tmp1][tmp2]=tmpmean;
            ij_count--;
            }

/* removed in favor of while looping...
        for (ig=ig_start;ig<=row-1-AA_rad;ig=ig+AA_step) {
            for (jg=jg_start;jg<=column-1-AA_rad;jg=jg+AA_step) {
                (void) fgets(line, sizeof(line), mean_sigma_file);
                line[strlen(line)-1]='\0';
                (void) sscanf(line,"%d %d %f",&tmp1,&tmp2,&tmpmean);
                mean_sigma_ptr[ig][jg]=tmpmean;
                ij_count++;
            }
        }

(void) printf("Last %d %d %f\n",tmp1,tmp2,mean_sigma_ptr[tmp1][tmp2]);
        (void) printf("last ig jg = %d %d \n",ig,jg);
*/
        (void) printf("lines should be %d and are %d\n",line_max,ij_count);
        (void) printf("\n");
        (void) printf("Mean read and assigned\n");
        (void) fprintf(mean_sigma_image_file, "P5\n");
        (void) fprintf(mean_sigma_image_file,"%d %d\n",
                column,row);
        (void) fprintf(mean_sigma_image_file,"255\n");
    }

(void) printf("Creating sigma's images\n");

/***** Write image files of sigma and I bar and I *****/

(void) fprintf(sigma_image_file,"P5\n");
    (void) fprintf(sigma_image_file,"%d %d\n",
                column,row);
    (void) fprintf(sigma_image_file,"255\n");

(void) printf("Image files' headers written.\n");

for (row_index=0;row_index<=row-1;row_index=row_index+1) {
        for (col_index=0;col_index<=column-1;col_index=col_index+1) {
        if (row_index < AA_rad | row_index >row-1-AA_rad-(int)(pixel_per_mm/
            2.0) | col_index < AA_rad | col_index >column-1-AA_rad-
            (int)(pixel_per_mm/2.0))
            temp_char=128;
        else {
            ig = (int)(pixel_per_mm)*(int)((row_index+(int)(pixel_per_mm/2))/
                (int)pixel_per_mm);
            jg = (int)(pixel_per_mm)*(int)((col_index+(int)(pixel_per_mm/2))/
                (int)pixel_per_mm);
            temp_char=(unsigned char)(sigma_ptr[ig][jg]*10);
        }
        (void) fputc(temp_char,sigma_image_file);
        }
    } if (mean_use == 1) {
        for (row_index=0;row_index<=row-1;row_index=row_index-1) {
            for (col_index=0;col_index<=column-1;col_index=col_index+1) {
            if (row_index < AA_rad | row_index >row-1-AA_rad-(int)(pixel_per_mm/
                2.0) | col_index < AA_rad | col_index >column-1-AA_rad-
                (int)(pixel_per_mm/2.0))
```

```
            temp_char=128;
        else {
            ig = (int)(pixel_per_mm)*(int)((row_index+(int)(pixel_per_mm/2))/
                    (int)pixel_per_mm);
            jg = (int)(pixel_per_mm)*(int)((col_index+(int)(pixel_per_mm/2))/
                    (int)pixel_per_mm);
            temp_char=(unsigned char)(mean_sigma_ptr[ig][jg]*10);
        }

(void) fputc(temp_char,mean_sigma_image_file);
        }
    }
}

/**********************************************************************/
/* NOW, we can compute the SNR1 values for all defined pixel locations  */
/* The math used here is basic subtraction and division with the results */
/* stored in a two-dimensional floating point data structure, contrast_ptr */
/**********************************************************************/
    (void) printf("Beginning contrast calculations...\n");

/***** defining allowed pixel locations, the "pixel_per_mm/2" factor is
        necessary to prevent row_k and row_l from extending into undefined
        pixel locations, and this defines the upper limit of "defined"
        pixel locations *****/
    for (row_index=AA_rad;row_index<=row-1-AA_rad-(int)(pixel_per_mm/2);
            row_index=row_index+1) {
        for (col_index=AA_rad;col_index<=column-1-AA_rad-(int)(pixel_per_mm/2);
                col_index=col_index+1) {
/***** need to parameterize the indices for the background information because
        we used a grid system to find sigma values, but used "all" pixel
        locations to find "I" and "I bar"  Grid points are a subset of "all"
        pixel locations *****/
            row_k = (int)(pixel_per_mm)*(int)((row_index+(int)(pixel_per_mm/2))/
                    (int)pixel_per_mm);
            col_l = (int)(pixel_per_mm)*(int)((col_index+(int)(pixel_per_mm/2))/
                    (int)pixel_per_mm);

/***** compute SNR1, contrast_ptr, using "all" pixel locations for "I" and
        "I bar", but using the parameterized "grid" points for sigma *****/
            if (mean_use == 1) {
                contrast_ptr[row_index][col_index] = (float)((target_avg_ptr
                            [row_index][col_index] - target_two_ptr
                            [row_index][col_index])/(sqrt(2.0)*
                            mean_sigma_ptr[row_k][col_l]));
            }
            else {
                contrast_ptr[row_index][col_index] = (float)((target_avg_ptr
                            [row_index][col_index] - target_two_ptr
                            [row_index][col_index])/(sqrt(2.0)*
                            sigma_ptr[row_k][col_l]));
            } if (contrast_ptr[row_index][col_index] < con_min) {
                con_min = contrast_ptr[row_index][col_index];
            }
            if (contrast_ptr[row_index][col_index] > con_max) {
                con_max = contrast_ptr[row_index][col_index];
                row_temp = row_index;
                col_temp = col_index;
            }
            if (mean_use == 1) {
                if (mean_sigma_ptr[row_k][col_l] < 0.0001) {
                    (void) printf("Warning***meansigma=%f at %d,%d\n",
                            mean_sigma_ptr[row_k][col_l],row_k,col_l);
                }
```

```c
            }
        } /* end col_index loop */
    } /* end row_index loop */

(void) printf("Writing information to files\n");

(void) fprintf(output1_file,"AA_rad = %d, AA_step = %d\n",
                AA_rad,AA_step);
    (void) fprintf(output1_file,"SS_rad = %d, SS_step = %d\n",
                SS_rad,SS_step);
    (void) fprintf(output1_file,"histo_size = %d, pixel_per_mm = %f\n",
                histo_size,pixel_per_mm);

row_k = 0;
    for (row_index=ig_start;row_index<=row-1-AA_rad;row_index=row_index+1) {
        col_l = 0;
        for (col_index=jg_start;col_index<=column-1-AA_rad;
                col_index=col_index+1) {
            if (sigma_ptr[row_index][col_index] < 0.0 | sigma_ptr[row_index]
                [col_index] > 0.0)
                (void) fprintf(sigma_file,"%d %d %f\n",
                            row_index,col_index,sigma_ptr[row_index][col_index]);
            col_l++;
        }
        row_k++;
    }

(void) printf("Creating picture of contrast-threshhold information.\n");
    contrast_file = fopen(CONTRAST_FILE_NAME, "w");
    if (contrast_file == NULL) {
        (void) printf("Can not open %s\n",CONTRAST_FILE_NAME);
        exit(8);
    }

(void) fprintf(contrast_file,"P5\n");
    (void) fprintf(contrast_file,"%d %d\n",
                column,row);
    (void) fprintf(contrast_file,"255\n");

for (row_index=0;row_index<=row-1;row_index=row_index+1) {
        for (col_index=0;col_index<=column-1;col_index=col_index+1) {
            if (row_index<AA_rad | row_index>row-1-AA_rad-(int)(pixel_per_mm/2.0) |
                col_index<AA_rad | col_index>column-1-AA_rad-(int)(pixel_per_mm/2.0))
                temp_char=128;
            else
                temp_char = (unsigned char)((contrast_ptr[row_index][col_index]
                            -con_min)*255/(con_max-con_min));
            (void) fputc(temp_char,contrast_file);
        }
    }
    (void) fclose(contrast_file);

(void) printf("The minimum SNR1 value is %f\n",con_min);
    (void) printf("The max SNR1 value is %f at row,column %d,%d\n",
                con_max,row_temp,col_temp);

if (positive == 1) {
        (void) printf("Threshhold cutoff, below which are no positive\n");
        (void) printf("contrast lesions is %f\n",thresh);
    }
    if (positive != 1) {
        (void) printf("Threshhold cutoff, above which are no negative\n");
        (void) printf("contrast lesions is %f\n",thresh);
    }

/****************************************************************/
```

```c
/* to create an image file, we need to write the three line header infor-  */
/* mation and the write the binary character information for each pixel    */
/* location. This particular image, will be the black and white image of   */
/* those pixels below/above the defined threshold value.                   */
/***************************************************************************/
    contrast_bw_file = fopen(CONTRAST_BW_FILE_NAME, "w");
    if (contrast_bw_file == NULL) {
        (void) printf("Can not open %s\n",CONTRAST_BW_FILE_NAME);
        exit(8);
    }
    (void) fprintf(contrast_bw_file,"P5\n");
    (void) fprintf(contrast_bw_file,"%d %d\n",
                   column,row);
    (void) fprintf(contrast_bw_file,"255\n");

/***** creating B/W image truly using ALL pixel location values, with those
       that fall outside the "all" defined locations be treated as "grey"
       or 128 in color ****/
    for (row_index=0;row_index<=row-1;row_index=row_index+1) {
        for (col_index=0;col_index<=column-1;col_index=col_index+1) {
            if (row_index < AA_rad | row_index >row-1-AA_rad-(int)(pixel_per_mm/
                2.0) | col_index < AA_rad | col_index >column-1-AA_rad-
                (int)(pixel_per_mm/2.0))
                temp_char=128;
            else
                if (positive == 1) { /* positive contrast */
                    if (contrast_ptr[row_index][col_index]>thresh)
                        temp_char=0;
                    else
                        temp_char=255;
                }
                else { /* negative contrast */
                    if (contrast_ptr[row_index][col_index]<thresh)
                        temp_char=0;
                    else
                        temp_char=255;
                }
            (void) fputc(temp_char,contrast_bw_file);
        }
    }

/***** write out a histogram of "hist_size" row averages for below thresh
       pixel values *****/

/*** computing the top section of the histogram ***/ for (row_index=AA_rad;row_index<= AA_rad+(int)(histo_size/2)-1;
         row_index=row_index+1) {
        temp_sum = 0.0;
        scale_increment = 0; /* used in scale_factor to track loop */
        for (i=AA_rad;i<=row_index+(int)(histo_size/2)-1;i++) {
            scale_increment=scale_increment+1;
            for (col_index=AA_rad;col_index<=column-1-AA_rad;
                 col_index=col_index+1) {
                if (positive == 1) { /*positive contrast*/
                    if (contrast_ptr[i][col_index]>thresh){
                        temp_sum = temp_sum++;
                    }
                    else {
                        temp_sum = temp_sum;
                    }
                }
                else { /* negative contrast */
                    if (contrast_ptr[i][col_index]<thresh){
                        temp_sum = temp_sum++;
                    }
```

```
                    else {
                        temp_sum = temp_sum;
                    }
                }
            } /* end col_index */
        } /* end i index */ scale_factor=(float)((float)histo_size/(float)(scale_increment));
        temp_sum=temp_sum*scale_factor;
        (void) fprintf(histogram_file,"%d %f %d\n",row_index,temp_sum,
                    scale_increment);
    } /* end row_index */

/***** computing middle section of histogram, use +/- symmetry about
        the particular histogram index *****/ for (row_index=AA_rad+(int)(histo_size/2);row_index<=
            row-AA_rad-(int)(histo_size/2);row_index=row_index+1) {
        temp_sum = 0.0;
        for (i=(int)(-histo_size/2);i<=(int)(histo_size/2)-1;i++) {
            for (col_index=AA_rad;col_index<=column-1-AA_rad;
                    col_index=col_index+1) {
                if (positive == 1) { /*positive contrast*/
                    if (contrast_ptr[row_index+i][col_index]>thresh){
                        temp_sum = temp_sum++;
                    }
                    else {
                        temp_sum = temp_sum;
                    }
                }
                else { /* negative contrast */
                    if (contrast_ptr[row_index+i][col_index]<thresh){
                        temp_sum = temp_sum++;
                    }
                    else {
                        temp_sum = temp_sum;
                    }
                }
            }
        }
        temp_sum = temp_sum;
        (void) fprintf(histogram_file,"%d %f\n",row_index,temp_sum);
    }

/*** computing the bottom section of the histogram ***/ for (row_index=row-AA_rad-(int)(histo_size/2)+1;row_index<=
            row-1-AA_rad;row_index=row_index+1) {
        temp_sum = 0.0;
        scale_increment = 0; /* used in scale factor to track loop */
        for (i=row_index-(int)(histo_size/2);i<=row-1-AA_rad;i++) {
            scale_increment=scale_increment+1;
            for (col_index=AA_rad;col_index<=column-1-AA_rad;
                    col_index=col_index+1) {
                if (positive == 1) { /*positive contrast*/
                    if (contrast_ptr[i][col_index]>thresh){
                        temp_sum = temp_sum++;
                    }
                    else {
                        temp_sum = temp_sum;
                    }
                }
                else { /* negative contrast */
                    if (contrast_ptr[i][col_index]<thresh){
                        temp_sum = temp_sum++;
```

```
            }
            else {
                temp_sum = temp_sum;
            }
        }
    }
    scale_factor = (float)((float)histo_size/(float)(scale_increment));
    temp_sum = temp_sum*scale_factor;
    (void) fprintf(histogram_file,"%d %f %d\n",row_index,temp_sum,
                scale_increment);
}

(void) fprintf(i_bar_file,"P5\n");
(void) fprintf(i_bar_file,"%d %d\n",
            column,row);
(void) fprintf(i_bar_file,"255\n");
for (row_index=0;row_index<=row-1;row_index=row_index+1) {
    for (col_index=0;col_index<=column-1;col_index=col_index+1) {
        if (row_index < AA_rad | row_index >row-1-AA_rad-(int)(pixel_per_mm/
            2.0) | col_index < AA_rad | col_index >column-1-AA_rad-
                (int)(pixel_per_mm/2.0))
            temp_char=128;
        else
            temp_char=(unsigned char)target_two_ptr[row_index][col_index];

(void) fputc(temp_char,i_bar_file);
    }
}

(void) fprintf(i_file,"P5\n");
(void) fprintf(i_file,"%d %d\n",
            column,row);
(void) fprintf(i_file,"255\n");
for (row_index=0;row_index<=row-1;row_index=row_index+1) {
    for (col_index=0;col_index<=column-1;col_index=col_index+1) {
        if (row_index < AA_rad | row_index >row-1-AA_rad-(int)(pixel_per_mm/
            2.0) | col_index < AA_rad | col_index >column-1-AA_rad-
                (int)(pixel_per_mm/2.0))
            temp_char=128;
        else
            temp_char=(unsigned char)target_avg_ptr[row_index][col_index];

(void) fputc(temp_char,i_file);
    }
}

(void) printf("Closing files and ending program...\n");
(void) fclose(contrast_bw_file);
(void) fclose(background_file);
(void) fclose(target_file);
(void) fclose(sigma_file);
(void) fclose(output_file);
(void) fclose(histogram_file);
(void) fclose(sigma_image_file);
(void) fclose(i_bar_file);
(void) fclose(i_file);
if (mean_use == 1) {
    (void) fclose(mean_sigma_image_file);
}
return(0);
}
/***** END of program *****/
```

It is understood that the present invention is not limited to the particular embodiments described above, but embraces all such modified forms thereof as come within the scope of the following claims.

What is claimed is:

1. An automated system for testing the resolution capabilities of ultrasound scanners, comprising:
   (a) means for storing digitized target slice image data of an ultrasound image corresponding to a slice whose midplane is superimposed on a plane of an ultrasound phantom which contains the centers of an array of target spheres and for storing digitized background slice image data of an ultrasound image corresponding to a slice of the ultrasound phantom which contains only background material;
   (b) means for retrieving the stored target slice and background slice image data for analysis;
   (c) means for calculating a lesion signal to noise ratio $(SNR)_L$ at each defined pixel location (j,k) in the target slice image using an average target slice pixel value $S_L$ calculated from image data over a sample area centered at the pixel location (j,k) in the target slice image, an average background pixel value $S_{MB}$ calculated from image data over a first averaging area centered at the pixel location (j,k) and including mostly background image data, and an average background plane pixel value standard deviation $\sigma_B$ calculated from image data over a second averaging area including the pixel location (j,k) in the background slice image;
   (d) means for determining the number of pixel locations in a sample depth range for which the absolute value of the lesion signal to noise ratio exceeds a first threshold value;
   (e) means for automatically determining a depth range limit of detectability by determining the sample depth range at which the number of pixel locations in the sample depth range where the absolute value of the lesion signal to noise ratio exceeds the first threshold value exceeds a second threshold value; and
   (f) means for displaying the depth range limit of detectability.

2. The automated system of claim 1 wherein the average background pixel value $S_{MB}$ is calculated from image data over an averaging area centered at the pixel location (j,k) in the target slice image.

3. The automated system of claim 1 wherein the lesion signal to noise ratio is calculated in accordance with the equation:

$$SNRL(j,k) \pm (S_L(j,k) - S_{MB}(j,k))/(2^{1/2})\sigma_B(j,k) \qquad (6).$$

4. The automated system of claim 1 wherein the defined pixel locations are all pixel locations in the target plane image for which an averaging area centered on the pixel location is contained entirely within the target image plane.

5. The automated system of claim 1 wherein the sample area is a square area of a side approximately ⅔ times a diameter of the target spheres in the array of target spheres.

6. The automated system of claim 1 wherein the first and second averaging areas are approximately 1 centimeter square areas.

7. The automated system of claim 1 wherein the standard deviation $\sigma_B$ is calculated as a standard error of the estimate which quantifies pixel value deviations from a 2-D surface fit of the pixel value data over the second averaging area.

8. The automated system of claim 1 additionally comprising means for digitizing the ultrasound image corresponding to a slice centered on the plane containing the centers of the array of test spheres to form the digitized target slice image data and for digitizing the ultrasound image corresponding to a slice containing only the background material to form the digitized background slice image data.

9. An automated system for testing the resolution capabilities of ultrasound scanners, comprising:
   (a) an ultrasound phantom including an ultrasound phantom container, a tissue mimicking background material contained within the phantom container, and at least one array of target spheres having coplanar centers enclosed by the background material wherein each target sphere in the array has approximately a same diameter and a same ultrasonic backscatter coefficient as other test spheres in the array and wherein the ultrasonic backscatter coefficient of each target sphere is different from a background ultrasonic backscatter coefficient of the background material;
   (b) means for digitizing an ultrasound image of the phantom corresponding to a scan slice centered on a plane in which the array of test sphere centers is coplanar to form digital target slice image data and for digitizing an ultrasound image of the phantom corresponding to a scan slice of the background material containing no test spheres to form digitized background slice image data;
   (c) means for storing the digitized target slice image data and the digitized background slice image data;
   (d) means for retrieving the stored target slice and background slice image data for analysis; and
   (e) means for calculating a lesion signal to noise ratio $(SNR)_L$ at each defined pixel location (j,k) in the target slice image using an average target slice pixel value $S_L$ calculated from image data over a sample area centered in the target slice image at the location (j,k), an average background pixel value $S_{MB}$ calculated from image data over a first averaging area centered at the pixel location (j,k) and including mostly background image data, and an average background slice pixel value standard deviation $\sigma_B$ calculated from image data over a second averaging area in the background slice image including the pixel location (j,k).

10. The automated system of claim 9 wherein the array of coplanar target sphere centers is a regular array.

11. The automated system of claim 9 wherein there are at least seven target spheres per centimeter of depth of the array of target spheres.

12. The automated system of claim 9 wherein the average background pixel value $S_{MB}$ is calculated from image data over an averaging area centered at the pixel location (j,k) in the target slice image.

13. The automated system of claim 9 wherein the lesion signal to noise ratio is calculated in accordance with the equation:

$$SNRL(j,k) \equiv (S_L(j,k) - S_{MB}(j,k))/(2^{1/2})\sigma_B(j,k) \qquad (6)$$

14. The automated system of claim 9 wherein the defined pixel locations are all pixel locations in the target slice image for which an averaging area centered on the pixel location is contained entirely within the target slice image.

15. The automated system of claim 9 wherein the sample area is a square area of a side approximately ⅔ times the diameter of the target spheres in the array of target spheres.

16. The automated system of claim 9 wherein the first and second averaging areas are approximately 1 centimeter square areas.

17. The automated system of claim 9 wherein the standard deviation $\sigma_B$ is calculated as a standard error of the estimate which quantifies pixel value deviations from a 2-D surface fit of the pixel value data over the second averaging area.

18. The automated system of claim 9 additionally comprising means for determining the number of pixel locations in a sample depth range for which the absolute value of the lesion signal to noise ratio exceeds a first threshold value.

19. The automated system of claim 18 additionally comprising means for automatically determining a depth range limit of detectability by determining the sample depth range at which the number of pixel locations in the sample depth range whose lesion signal to noise ratio absolute values exceed the first threshold value exceeds a second threshold value.

20. A method for testing the resolution of ultrasound scanners, comprising the steps of:
(a) taking a first ultrasound image having a scan slice centered on a plane of an ultrasound phantom containing an array of target spheres with coplanar centers;
(b) digitizing the first ultrasound image to form digitized target slice image data;
(c) taking a second ultrasound image having a scan slice containing a background material and no target spheres;
(d) digitizing the second ultrasound image to form digitized background slice image data;
(e) storing the target slice and background slice image data;
(f) retrieving the target slice and background slice image data for analysis;
(g) calculating a lesion signal to noise ratio (SNR) at each defined pixel locations (j,k) in the target slice image using an average target slice image pixel value $S_L$ calculated from image data over a sample area centered in the target slice image at the location (j,k), an average background pixel value $S_{MB}$ calculated from image data over a first averaging area centered at the pixel location (j,k) and an average background slice image pixel value standard deviation $\sigma_B$ calculated from image data over a second averaging area in the background slice image including the pixel location (j,k).

21. The method of claim 20 wherein the average background pixel value $S_{MB}$ is calculated from image data over an averaging area centered at pixel location (j,k) in the target slice image.

22. The method of claim 20 wherein the lesion signal to noise ratio is calculated in accordance with the equation:

$$SNR_{L\,(j,k)} \equiv (S_L(j,k)) - S_{MB}(j,k))/(2^{1/2})\sigma_B(j,k) \qquad (6).$$

23. The method of claim 20 wherein the defined pixel locations are all pixel locations in the target slice image for which an averaging area centered on the pixel location is contained entirely within the target slice image.

24. The method of claim 20 wherein the sample area is a square area of a side approximately ⅔ times the diameter of the target spheres in the array of target spheres.

25. The method of claim 20 wherein the first and second averaging areas are approximately 1 centimeter square areas.

26. The method of claim 20 wherein the second averaging area is centered at the pixel location (j,k) in the digitized background slice image.

27. The method of claim 20 wherein the standard deviation $\sigma_B$ is calculated as a standard error of the estimate which quantifies pixel value deviations from a 2-D surface fit of the pixel value data over the second averaging area.

28. The method of claim 20 further comprising the additional step of determining the number of pixel locations in a sample depth range for which the absolute value of the lesion signal to noise ratio exceeds a first threshold value.

29. The method of claim 28 further comprising the additional step of automatically determining a depth range limit of detectability by determining the sample depth range at which the number of pixel locations in the sample depth range whose lesion signal to noise ratio absolute values exceed the first threshold value exceeds a second threshold value.

* * * * *

UNITED STATES PATENT AND TRADEMARK OFFICE
CERTIFICATE OF CORRECTION

PATENT NO. : 5,574,212                                    Page 1 of 2
DATED      : November 12, 1996
INVENTOR(S): Ernest L. Madsen; James A. Zagzebski; Gary R. Frank;
             Jason J. Rownd It is certified that error appears in the above-indentified patent and that said Letters Patent is hereby corrected as shown below:

In column 1, line 5 of the patent, after the title and before "FIELD OF THE INVENTION", insert --A portion of the disclosure of this patent document contains material which is subject to copyright protection. The copyright owner has no objection to the facsimile reproduction by anyone of the patent document or patent disclosure as it appears on the Patent and Trademark Office patent file or records, but otherwise reserves all copyright rights whatsoever--.

In column 4, line 23 of the patent, "$P_m$" should be --$P^m$--.

In column 13, Equation 6 of the patent,
"$SNRL(j,k) = (S_L(j,k)) - S_{MB}(j,k))/(2^{1/2})\sigma_B(j,k)$" should be --$SNR_{L(j,k)} = (S_L(j,k) - S_{MB}(j,k))/(2^{1/2})\sigma_B(j,k)$--.

In column 14, line 31 of the patent, "$\sigma_{MB}$" should be -$\sigma_B$--.

In column 49, Claim 3, Equation 6 of the patent,
"$SNRL(j,k) \pm (S_L(j,k)) - S_{MB}(j,k))/(2^{1/2})\sigma_B(j,k)$" should be --$SNR_{L(j,k)} \equiv (S_L(j,k) - S_{MB}(j,k))/(2^{1/2})\sigma_B(j,k)$--.

UNITED STATES PATENT AND TRADEMARK OFFICE
CERTIFICATE OF CORRECTION

PATENT NO. : 5,574,212
DATED : November 12, 1996
INVENTOR(S) : Ernest L. Madsen; James A. Zagzebski; Gary R. Frank; Jason J. Rownd It is certified that error appears in the above-indentified patent and that said Letters Patent is hereby corrected as shown below:

In column 50, Claim 13, Equation 6 of the patent,
"$SNRL(j,k) \equiv (S_L(j,k)) - S_{MB}(j,k))/(2^{1/2}))\sigma_B(j,k)$" should be -- $SNR_{L(j,k)} \equiv (S_L(j,k) - S_{MB}(j,k))/(2^{1/2})\sigma_B(j,k)$ --.

In column 52, Claim 22, Equation 6 of the patent,
"$SNR_{L(j,k)} \equiv (S_L(j,k)) - S_{MB}(j,k)/(2^{1/2})\sigma_B(j,k)$" should be
-- $SNR_{L(j,k)} \equiv (S_L(j,k) - S_{MB}(j,k))/(2^{1/2})\sigma_B(j,k)$ --

Signed and Sealed this

Third Day of March, 1998

Attest:

BRUCE LEHMAN

*Attesting Officer*   *Commissioner of Patents and Trademarks*